(12) United States Patent
Sato et al.

(10) Patent No.: US 9,874,518 B2
(45) Date of Patent: Jan. 23, 2018

(54) OPTICAL SENSOR SYSTEM, OPTICAL GAS SENSOR SYSTEM, PARTICULATE SENSOR SYSTEM, LIGHT EMITTING APPARATUS, AND IMAGE PRINTING APPARATUS

(71) Applicant: Sharp Kabushiki Kaisha, Sakai, Osaka (JP)

(72) Inventors: Takanobu Sato, Osaka (JP); Noboru Iwata, Osaka (JP); Tazuko Kitazawa, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/122,516

(22) PCT Filed: Mar. 24, 2015

(86) PCT No.: PCT/JP2015/058921
§ 371 (c)(1),
(2) Date: Aug. 30, 2016

(87) PCT Pub. No.: WO2015/163074
PCT Pub. Date: Oct. 29, 2015

(65) Prior Publication Data
US 2017/0067825 A1    Mar. 9, 2017

(30) Foreign Application Priority Data

Apr. 22, 2014 (JP) .................................. 2014-088332

(51) Int. Cl.
*G01J 3/00* (2006.01)
*H01S 5/068* (2006.01)
(Continued)

(52) U.S. Cl.
CPC ............. *G01N 21/53* (2013.01); *G01N 21/61* (2013.01); *G01N 21/77* (2013.01); *G03G 15/043* (2013.01);
(Continued)

(58) Field of Classification Search
CPC ................... G01N 21/53; G01N 21/61; G01N 2201/0612; H01S 5/06804; H01S 5/0028; G03G 15/043
See application file for complete search history.

(56) References Cited

U.S. PATENT DOCUMENTS 5,031,059 A * 7/1991 Yamaguchi .......... G11B 17/038
                                                  360/97.17
6,947,138 B2 * 9/2005 Arno ...................... G01N 21/78
                                                  356/437
(Continued)

FOREIGN PATENT DOCUMENTS

JP    S59-105568 A    6/1984
JP    S6179285 A    4/1986
(Continued)

OTHER PUBLICATIONS

International Search Report of PCT/JP2015/058921 dated Jun. 23, 2015.

*Primary Examiner* — Sang Nguyen
(74) *Attorney, Agent, or Firm* — ScienBiziP, P.C.

(57) ABSTRACT

An optical sensor system is provided which can be used not only as an ordinary light source, but also to calculate an environmental parameter. Rear surface outgoing light (31) output from a rear surface (21) of a semiconductor laser (10) is used in a process of calculating an environmental parameter by control and arithmetic device (60) to, while front
(Continued)

surface outgoing light (30) output from a front surface (20) is used in an application other than the calculation of the environmental parameter.

17 Claims, 9 Drawing Sheets

(51) Int. Cl.
| | | |
|---|---|---|
| *H01S 5/00* | (2006.01) | |
| *G01N 21/53* | (2006.01) | |
| *G01N 21/63* | (2006.01) | |
| *G01N 21/61* | (2006.01) | |
| *G03G 15/043* | (2006.01) | |
| *G01N 21/77* | (2006.01) | |
| *H01S 5/0683* | (2006.01) | |

(52) U.S. Cl.
CPC .......... *H01S 5/0014* (2013.01); *H01S 5/0028* (2013.01); *G01N 2021/7773* (2013.01); *G01N 2021/7776* (2013.01); *G01N 2021/7783* (2013.01); *G01N 2201/0612* (2013.01); *H01S 5/0683* (2013.01); *H01S 5/06804* (2013.01)

(56) References Cited

U.S. PATENT DOCUMENTS

| | | | |
|---|---|---|---|
| 2001/0019563 A1* | 9/2001 | Hatori | H01S 5/141 372/21 |
| 2003/0058907 A1* | 3/2003 | Nasu | H01S 5/02208 372/34 |
| 2003/0081309 A1* | 5/2003 | Nishi | H01S 5/0687 359/337.2 |
| 2005/0163017 A1* | 7/2005 | Taniguchi | G11B 7/127 369/112.01 |
| 2012/0057161 A1* | 3/2012 | Tkachuk | G01N 21/3504 356/437 |
| 2015/0139451 A1 | 5/2015 | Fischer et al. | |

FOREIGN PATENT DOCUMENTS

| | | |
|---|---|---|
| JP | H0666721 A | 3/1994 |
| JP | H0669607 A | 3/1994 |
| JP | H1117230 A | 1/1999 |
| JP | 2009204935 A | 9/2009 |
| JP | 2013117736 A | 6/2013 |
| WO | 2012163681 A1 | 12/2012 |

* cited by examiner

OPTICAL SENSOR SYSTEM, OPTICAL GAS SENSOR SYSTEM, PARTICULATE SENSOR SYSTEM, LIGHT EMITTING APPARATUS, AND IMAGE PRINTING APPARATUS

TECHNICAL FIELD

The present invention relates to an optical sensor system, an optical gas sensor system, a particulate sensor system, a light emitting apparatus, and an image printing apparatus.

BACKGROUND ART

Semiconductor lasers are used in various application fields for the reason that the semiconductor laser is able to emit coherent laser light with high directivity, and that it is small in size and inexpensive.

The semiconductor laser is constituted by two mirror surfaces positioned to face each other, and a waveguide disposed between the two mirror surfaces. When a current is injected into the semiconductor laser, photons are generated in the waveguide. The generated photons are reflected by the two mirror surfaces to repeatedly reciprocate inside the waveguide such that the number of photons increases in a chain relation and the photons eventually reach a resonant state. There is a difference in reflectance between the two mirror surfaces, and stronger laser light is emitted from the mirror surface having a lower reflectance (higher transmittance). Generally, the stronger laser light is used in various application fields.

On the other hand, laser light having a comparatively low output power is also emitted from the mirror surface having a higher reflectance (lower transmittance). The weaker laser light is generally not used at all or just used as reference information for an output power of the laser light that is emitted from the mirror surface having the lower reflectance. In the latter case, the laser light emitted from the mirror surface having the higher reflectance is monitored by employing a photodiode.

In order to utilize the laser light emitted from the semiconductor laser in various application fields, it is very important to know at least one environmental parameter (e.g., temperature, humidity, or gas concentration), which represents the state of an environment around the semiconductor laser.

Patent Literature (PTL) 1, for example, discloses a technique of predicting the degradation status of a semiconductor laser or avoiding an abrupt failure by continuously monitoring humidity inside a container with a humidity sensor disposed within the container in which an encapsulated semiconductor laser is also disposed.

PTLs 2 to 4 disclose techniques of determining whether dew condensation occurs on a semiconductor laser, or avoiding the occurrence of dew condensation by monitoring temperature and humidity around the semiconductor laser or around an apparatus onto which the semiconductor laser is mounted, with a temperature sensor and a humidity sensor, respectively.

CITATION LIST

Patent Literature

PTL 1: Japanese Unexamined Patent Application Publication No. 11-17230 (Laid-Open on Jan. 22, 1999)
PTL 2: Japanese Unexamined Patent Application Publication No. 61-79285 (Laid-Open on Apr. 22, 1986)
PTL 3: Japanese Unexamined Patent Application Publication No. 2009-204935 (Laid-Open on Sep. 10, 2009)
PTL 4: Japanese Unexamined Patent Application Publication No. 2013-117736 (Laid-Open on Jun. 13, 2013)

SUMMARY OF INVENTION

Technical Problem

However, the above techniques disclosed in PTLs 1 to 4 have a problem that costs of the various sensors used for measuring the environmental parameters are high. Another problem is that because a space for installation of the various sensors is needed within the apparatus onto which the semiconductor laser is mounted, it is difficult to reduce the size of the apparatus.

The present invention has been made in view of the above-described situations, and an object of the present invention is to provide an optical sensor system that can be used not only as an ordinary light source, but also to calculate an environmental parameter.

Solution to Problem

To solve the above-described problems, according to one aspect of the present invention, there is provided an optical sensor system including a light emitting device that generates first emission light for use in a predetermined application, the light emitting device further generating second emission light, wherein the optical sensor system further includes an emission light detector that detects the second emission light, and an environmental parameter calculation unit that calculates an environmental parameter, as an index of an environment around the light emitting device, by employing a value of the second emission light detected by the emission light detector.

According to another aspect of the present invention, there is provided an optical sensor system including a light emitting device that generates first emission light and second emission light, the optical sensor system further including an emission light detector that detects the second emission light, and an environmental parameter calculation unit that calculates an environmental parameter, as an index of an environment around the light emitting device, by employing a value of the second emission light detected by the emission light detector, wherein the light emitting device includes a first light emitting surface from which the first emission light is output, and a second light emitting surface from which the second emission light is output, and the first light emitting surface and the second light emitting surface are constituted such that, when the environmental parameter has changed, a change rate of intensity of the first emission light is smaller than a change rate of intensity of the second emission light.

Advantageous Effects of Invention

According to one aspect of the present invention, the optical sensor system can be used not only as an ordinary light source, but also to calculate the environmental parameter.

DESCRIPTION OF EMBODIMENTS

Embodiments of the present invention will be described below.

Embodiment 1

The optical sensor system 1 according to one embodiment of the present invention is described below with reference to FIGS. 1 and 2. The optical sensor system 1 includes a semiconductor laser 10 (light emitting device) and emits laser light that can be used in various application fields. Furthermore, the optical sensor system 1 is able to detect an environmental parameter. The term "environmental parameter" implies a parameter serving as an index for an environment of the optical sensor system 1. The environmental parameter is at least one of temperature, humidity, and gas concentration, for example, in the environment around the optical sensor system 1.

In this embodiment, the optical sensor system 1 detects humidity as the environmental parameter. In other words, in this embodiment, humidity is a target of sensing carried out by the optical sensor system 1.

[Configuration of Optical Sensor System 1]

Figure 1:
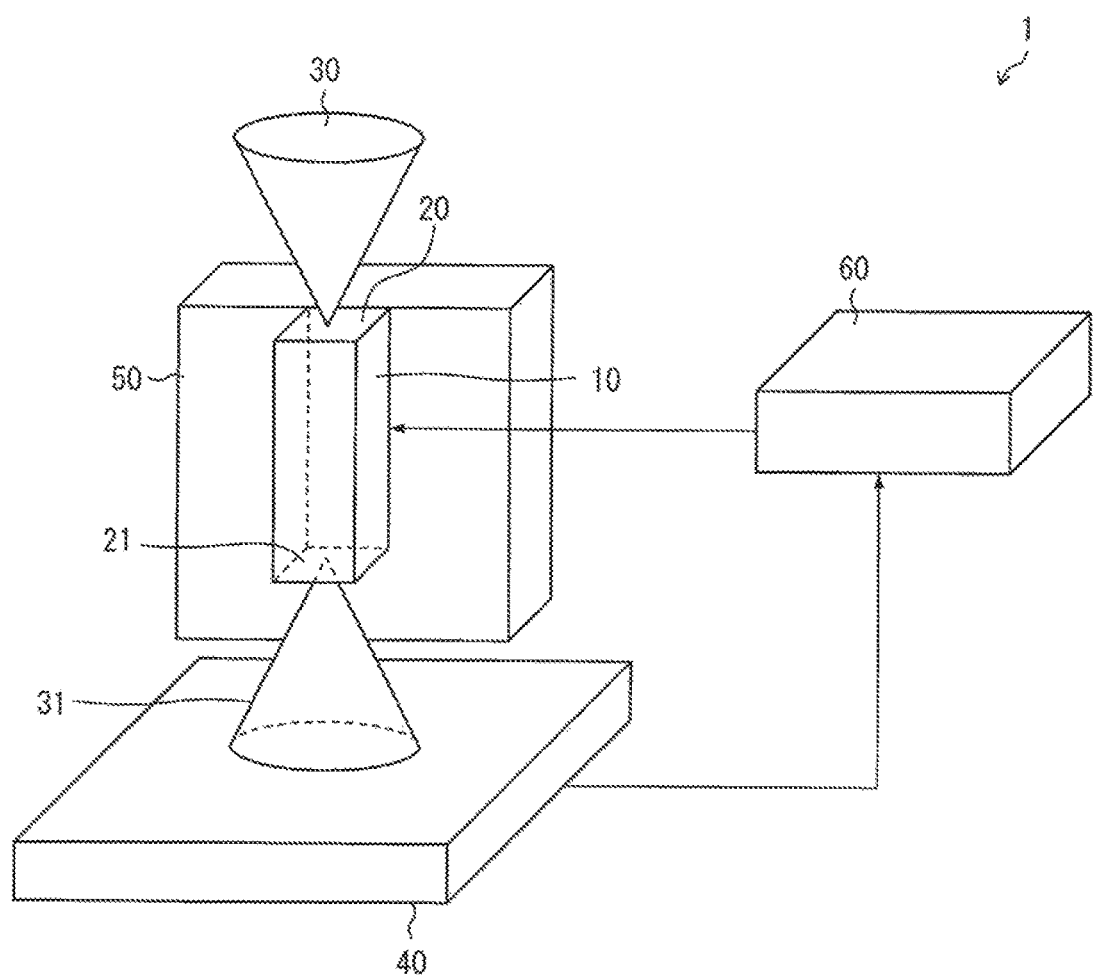
FIG. 1 is a schematic view illustrating a basic configuration of an optical sensor system according to Embodiment 1 of the present invention.

FIG. 1 is a schematic view illustrating a basic configuration of the optical sensor system 1. As illustrated in FIG. 1, the optical sensor system 1 includes the semiconductor laser 10, a photodiode 40 (emission light detector), a sub-mount 50, and a control and arithmetic device 60 (environmental parameter calculation unit).

The semiconductor laser 10 is an element that emits the laser light with injection of a current. Because the semiconductor laser is generally small in size and inexpensive, it is suitable as a light source in the optical sensor system 1 of the present invention. As illustrated in FIG. 1, the semiconductor laser 10 has a front surface 20 (first light emitting surface) and a rear surface 21 (second light emitting surface). The front surface 20 and the rear surface 21 are each a mirror surface. A waveguide (not illustrated) is formed between the front surface 20 and the rear surface 21.

The front surface 20 has a lower reflectance and a higher transmittance than the rear surface 21. Therefore, the intensity of front surface outgoing light 30 (first emission light) output from the front surface 20 is larger than that of rear surface outgoing light 31 (second emission light) output from the rear surface 21. The stronger front surface outgoing light 30 output from the front surface 20 is used in various application fields. It is to be noted that the optical sensor system 1 may include a different type of light source (e.g., a fluorescent lamp, an LED, or a HID lamp) instead of the semiconductor laser 10. In such a case, the different type of light source may emit two kinds of lights (i.e., the front surface outgoing light 30 and the rear surface outgoing light 31) in turn from one light emitting surface. Alternatively, the different type of light source may branch one beam of light, which is emitted from one light emitting surface, into the two beams of lights.

The current injected into the semiconductor laser 10 acts to generate photons in the waveguide. The generated photons are reflected by the front surface 20 and the rear surface 21 to repeatedly reciprocate inside the waveguide such that the number of photons inside the waveguide increases in a chain relation and the photons eventually reach a resonant state. When the photons inside the waveguide reach the resonant state, the front surface outgoing light 30 and the rear surface outgoing light 31 are output from the front surface 20 and the rear surface 21, respectively.

The front surface outgoing light 30 output from the front surface 20 is used as a laser light source in various application fields. The rear surface outgoing light 31 output from the rear surface 21 is input to a photodiode 40.

The photodiode 40 is an element for detecting the rear surface outgoing light 31 input thereto, and for converting a detected value of the rear surface outgoing light 31 to an electrical signal (current signal or voltage signal). The photodiode 40 sends the electrical signal converted from the rear surface outgoing light 31 to the control and arithmetic device 60. In the optical sensor system 1, the photodiode 40 may be replaced with another means capable of evaluating the intensity of the rear surface outgoing light 31.

The sub-mount 50 has a role to fix the semiconductor laser 10 in place and to release heat generated from the semiconductor laser 10 to the exterior. A ceramic material having high thermal conductivity, e.g., aluminum nitride, is generally used as a material of the sub-mount 50. In general, the semiconductor laser 10 is bonded to the sub-mount 50 with a solder material, e.g., an Au—Sn alloy solder, interposed between them.

The control and arithmetic device 60 controls the semiconductor laser 10. Furthermore, the control and arithmetic device 60 calculates the environmental parameter (humidity) based on the amplitude of the electrical signal that has been received from the photodiode 40, (i.e., on the intensity of the rear surface outgoing light 31). The control and arithmetic device 60 may calculate, by way of example, the humidity on the basis of a relation between humidity and light intensity, the relation being previously stored in a storage device (not illustrated). The control and arithmetic device 60 can be constituted by a plurality of chips and a microcomputer. A general-purpose arithmetic device, such as a personal computer, may be used as the control and arithmetic device 60. One example of a method of calculating the environmental parameter by the control and arithmetic device 60 will be described below.

[Environmental Parameter Calculation Method 1]

One example of the method of calculating the environmental parameter (humidity) by the control and arithmetic device 60 is described. First, the control and arithmetic device 60 injects a constant current (under ACC) into the semiconductor laser 10, thus causing the semiconductor laser 10 to emit light. After the intensity of the light emitted from the semiconductor laser 10 has been stabilized, the control and arithmetic device 60 evaluates the intensity of the rear surface outgoing light 31 on the basis of the electrical signal received from the photodiode 40. Immediately after evaluating the intensity of the rear surface outgoing light 31, the control and arithmetic device 60 turns off the semiconductor laser 10. Then, the control and arithmetic device 60 calculates the humidity from an obtained evaluation value on the basis of a relation between humidity and light intensity (e.g., experimental data illustrated in FIG. 2), which has been previously stored in the storage device (not illustrated).

With a light emission time of the semiconductor laser 10 being longer, an amount of heat generated from the semiconductor laser 10 increases and the lifetime thereof shortens. In the method of calculating the environmental parameter, therefore, it is preferable that the light emission time of the semiconductor laser 10 is shorter.

In the method of calculating the environmental parameter, the control and arithmetic device 60 is not always required to drive the semiconductor laser 10 with the constant current (ACC). The control and arithmetic device 60 may drive the semiconductor laser 10 with a constant output power (APC) such that the intensity of the rear surface outgoing light 31 is kept constant. In such a case, the control and arithmetic device 60 calculates the humidity on the basis of a current value of the injection current injected into the semiconductor laser 10, when the intensity of the rear surface outgoing light 31 has reached a substantially constant state.

With the configuration of the optical sensor system 1, as described above, it is possible not only to use the front surface outgoing light 30 as an ordinary laser light source in various application fields, but also to calculate the environmental parameter on the basis of the intensity of the rear surface outgoing light 31 that is output in addition to the front surface outgoing light 30.

[Relation Between Humidity and Intensity of Laser Light]

A relation between the humidity around the semiconductor laser 10 and the intensity of each of the front surface outgoing light 30 and the rear surface outgoing light 31, which are both emitted from the semiconductor laser 10, is described below by employing experimental data.

In the experiment, the semiconductor laser 10 for use in an optical recording apparatus was employed. The employed semiconductor laser 10 had an oscillation wavelength of 660 nm and a maximum output power of 150 mW. The reflectance of the front surface 20 of the semiconductor laser 10 on the waveguide side and the reflectance of the rear surface 21 thereof on the waveguide side were designed respectively to about 6% (transmittance; about 94%) and about 90% (transmittance; about 10%).

The reflectance at each of end surfaces of the semiconductor laser 10 is specified by a multilayer structure of a multilayer film mirror that is formed on the each end surface. Thus, the reflectance of the end surface is different depending on the refractive indexes of materials constituting the multilayer structure and the number of the layers.

The intensity of the front surface outgoing light 30 output from the front surface 20 having a lower reflectance and a higher transmittance is stronger than that of the rear surface outgoing light 31 output from the rear surface 21 having a higher reflectance and a lower transmittance. In the optical recording apparatus, the front surface outgoing light 30 is used to record information on an optical storage medium, and to reproduce information from the optical storage medium.

Figure 2:
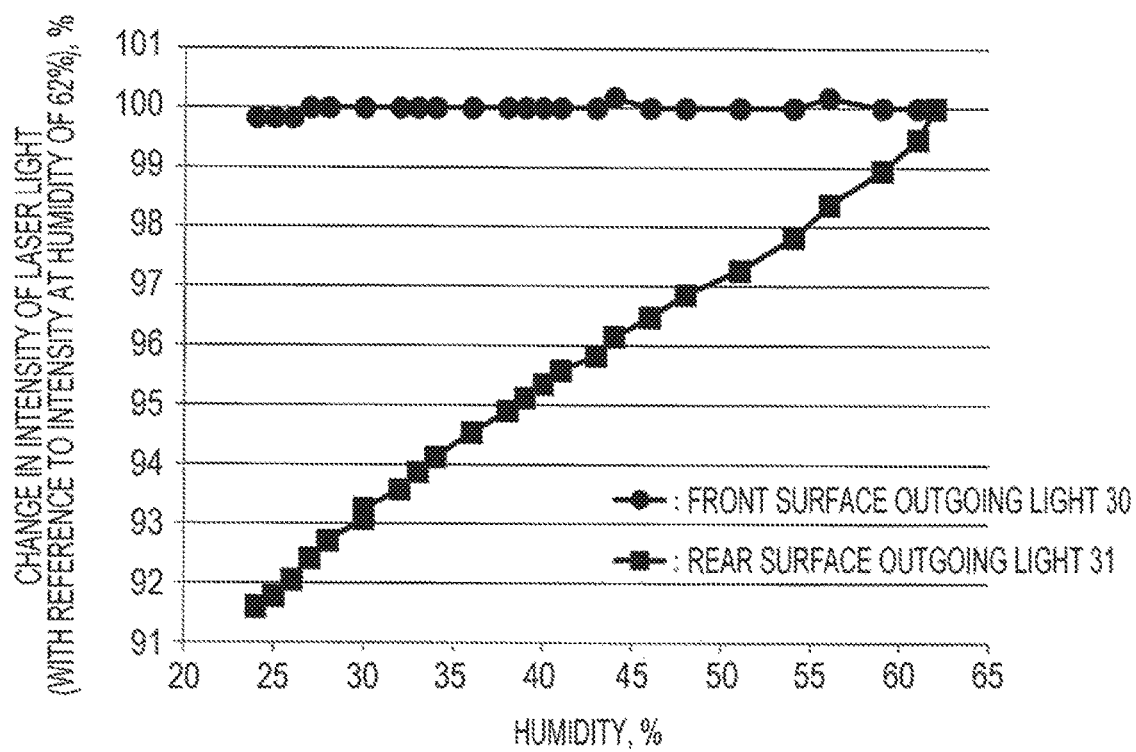
FIG. 2 plots experimental data representing a relation between humidity and intensity of each of front surface outgoing light and rear surface outgoing light, both the lights being emitted from a semiconductor laser that is included in the optical sensor system according to Embodiment 1 of the present invention.

FIG. 2 plots experimental data representing change in the intensity of each of the front surface outgoing light 30 and the rear surface outgoing light 31 with respect to change in humidity.

As plotted in FIG. 2, the humidity and the intensity of the rear surface outgoing light 31 have a substantially proportional relation. When the humidity increases from 23% to 62%, the intensity of the rear surface outgoing light 31 is increased about 8.7%. The control and arithmetic device 60 is able to calculate the humidity from the intensity of the rear surface outgoing light 31 by utilizing the proportional relation between the humidity and the intensity of the rear surface outgoing light 31.

On the other hand, as plotted in FIG. 2, the intensity of the front surface outgoing light 30 is substantially constant without depending on the humidity (difference between a maximum value and a minimum value of the intensity of the front surface outgoing light 30 is about 0.35%). A change amount (0.35%) of the intensity of the front surface outgoing light 30 is not more than $\frac{1}{20}$ of a change amount (8.7%) of the intensity of the rear surface outgoing light 31. Therefore, the front surface outgoing light 30 can be utilized in various applications, such as a field of recording or reproducing information with respect to an optical recording medium, with no necessity of considering an influence due to the change in the humidity.

The principle of the above-described responses of the front surface outgoing light 30 and the rear surface outgoing light 31 to the change in humidity is described below.

When the humidity around the semiconductor laser 10 changes, amounts of moisture adsorbed on the front surface 20 and the rear surface 21 at the open side (i.e., on both the surfaces at the side exposed to the exterior) also change. As a result, the refractive indexes of the front surface 20 and the rear surface 21 change. With the changes in the refractive indexes of the front surface 20 and the rear surface 21, the transmittances and the reflectances of those surfaces are changed.

As described above, the front surface 20 is designed to have the high transmittance (about 94%). Accordingly, when the transmittance of the front surface 20 slightly changes with the change in humidity, the intensity of the front surface outgoing light 30 is not so changed. Thus, when the humidity has changed, a change rate of the intensity of the front surface outgoing light 430 is small. On the other hand, as described above, the rear surface 21 is designed to have the low transmittance (about 10%). Accordingly, when the transmittance of the rear surface 21 slightly changes with the change in humidity, the intensity of the rear surface outgoing light 31 is changed to a large extent. Thus, when the humidity has changed, a change rate of the intensity of the rear surface outgoing light 31 is large.

In order to increase the change rate of the intensity of the rear surface outgoing light 31 with respect to the change in humidity, the rear surface 21 is preferably designed to have a higher reflectance. However, it is difficult to design the rear surface 21 having a so high reflectance. In addition, the manufacturing cost of the semiconductor laser 10 having the rear surface 21 with such a high reflectance increases. Thus, it is sufficient for the rear surface 21 to have the reflectance of not less than 85% from the viewpoint of facilitating the design of the rear surface 21 and reducing the cost of the semiconductor laser 10.

Embodiment 2

Another embodiment of the present invention will be described below with reference to FIG. 3. For convenience of explanation, members having the same functions as those described in the above embodiment are denoted by the same reference sings, and description of those members is omitted.

The light intensity of the semiconductor laser 10 changes depending on several factors, such as heat generation and deterioration. If the light intensity of the semiconductor laser 10 changes depending on those factors, the intensity of each of the front surface outgoing light 30 and the rear surface outgoing light 31 also changes.

In the environmental parameter calculation method 1 described in the above Embodiment 1, the change in the intensity of the rear surface outgoing light 31 depending on the above-mentioned factors is not taken into consideration. Accordingly, when the humidity (environmental parameter) is calculated on the basis of the intensity of the rear surface outgoing light 31, which has changed depending on the above-mentioned factors, there is a possibility that an error occurs in the calculated value of the humidity.

On the other hand, the intensity of the front surface outgoing light 30 does not depend on the humidity (see FIG. 2). It is hence thought that the intensity of the front surface outgoing light 30 depends on only the above-mentioned factors.

In view of the above point, a configuration for correcting the intensity of the rear surface outgoing light 31 by utilizing the intensity of the front surface outgoing light 30 is described in this embodiment. The following configuration can reduce an influence of the change in the intensity of the rear surface outgoing light 31, which is attributable to, e.g., heat generation and/or deterioration, upon the accuracy in calculating the environmental parameter, and can suppress an error of the environmental parameter.

[Configuration of Optical Sensor System 2]

Figure 3:
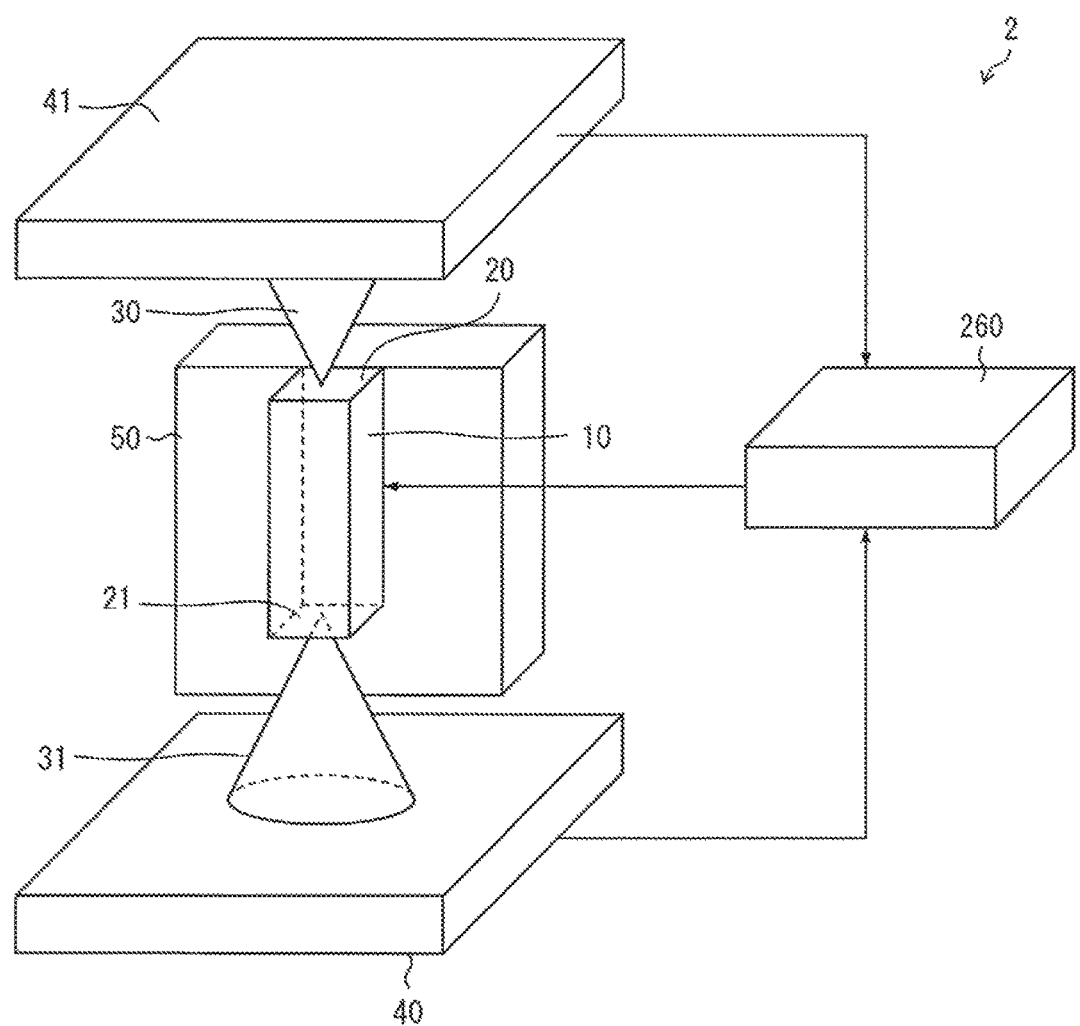
FIG. 3 is a schematic view illustrating a basic configuration of an optical sensor system according to Embodiment 2 of the present invention.

FIG. 3 is a schematic view illustrating a basic configuration of an optical sensor system 2 according to this embodiment. As illustrated in FIG. 3, the optical sensor system 2 includes the semiconductor laser 10, the photodiode 40, a second photodiode 41 (second detector), the sub-mount 50, and a control and arithmetic device 260.

Similarly to the photodiode 40 described in the above Embodiment 1, the second photodiode 41 detects the laser light input to the second photodiode 41 and converts a detected value of the laser light to an electrical signal. As illustrated in FIG. 3, the front surface outgoing light 30 output from the front surface 20 of the semiconductor laser 10 is input to the second photodiode 41. The second photodiode 41 converts a detected value of the front surface outgoing light 30 to an electrical signal (current signal or voltage signal), and sends the electrical signal to the control and arithmetic device 260.

The control and arithmetic device 260 controls the semiconductor laser 10. Furthermore, the control and arithmetic device 260 receives the electrical signal from each of the photodiode 40 and the second photodiode 41. The control and arithmetic device 260 can be constituted by a plurality of chips and a microcomputer. A general-purpose arithmetic device, such as a personal computer, may be used as the control and arithmetic device 260.

The control and arithmetic device 260 evaluates the intensity of the front surface outgoing light 30 from the amplitude of the electrical signal that has been detected by the second photodiode 41. The control and arithmetic device 260 further evaluates the intensity of the rear surface outgoing light 31 from the amplitude of the electrical signal that has been detected by the photodiode 40. Thereafter, the control and arithmetic device 260 corrects the intensity of the rear surface outgoing light 31 on the basis of the intensity of the front surface outgoing light 30. The control and arithmetic device 260 then calculates the environmental parameter (humidity) on the basis of the corrected intensity of the rear surface outgoing light 31. One example of a method of calculating the environmental parameter by the control and arithmetic device 260 will be described below.

[Environmental Parameter Calculation Method 2]

According to this method, a relation between a value resulting from dividing the intensity of the rear surface outgoing light 31 by the intensity of the front surface outgoing light 30 and humidity is evaluated in advance.

The control and arithmetic device 260 injects a certain amount of current into the semiconductor laser 10, thus causing the semiconductor laser 10 to emit light. After the intensity of the light emitted from the semiconductor laser 10 has been stabilized, the control and arithmetic device 260 evaluates the intensity of the rear surface outgoing light 31 on the basis of the electrical signal that has been received from the photodiode 40. Furthermore, the control and arithmetic device 260 evaluates the intensity of the front surface outgoing light 30 on the basis of the electrical signal that has been received from the second photodiode 41. After evaluating the intensity of the front surface outgoing light 30, the control and arithmetic device 260 turns off the semiconductor laser 10.

Next, the control and arithmetic device 260 calculates a ratio of the intensity of the rear surface outgoing light 31 to the intensity of the front surface outgoing light 30. When the light intensity of the semiconductor laser 10 changes depending on, e.g., heat generation and/or deterioration, the intensity of the front surface outgoing light 30 and the intensity of the rear surface outgoing light 31 are changed at the same proportion. Thus, the change attributable to the above-mentioned factors are eliminated from the intensity of the rear surface outgoing light 31 by dividing the intensity of the rear surface outgoing light 31 by the intensity of the front surface outgoing light 30. As a result, the intensity of the rear surface outgoing light 31 depending on only the humidity is obtained.

The control and arithmetic device 260 calculates the environmental parameter (humidity) on the basis of the value resulting from dividing the intensity of the rear surface outgoing light 31 by the intensity of the front surface outgoing light 30 with reference to the above-described relation (i.e., the relation between the value resulting from dividing the intensity of the rear surface outgoing light 31 by the intensity of the front surface outgoing light 30 and humidity).

[Environmental Parameter Calculation Method 3]

The control and arithmetic device 260 calculates the environmental parameter (humidity) by the following method, for example.

According to this method, a relation between the intensity of the rear surface outgoing light 31 and humidity when the intensity of the front surface outgoing light 30 is a predetermined value is evaluated in advance.

The control and arithmetic device 260 injects a current into the semiconductor laser 10, thus causing the semiconductor laser 10 to emit light, and evaluates the intensity of the front surface outgoing light 30 on the basis of the electrical signal that has been received from the second photodiode 41. Furthermore, the control and arithmetic device 260 controls a current value of the injection current, which is applied to the semiconductor laser 10, such that the intensity of the front surface outgoing light 30 is kept at the above-mentioned predetermined value.

The control and arithmetic device 260 evaluates the intensity of the rear surface outgoing light 31 on the basis of the electrical signal received from the photodiode 40 when the intensity of the front surface outgoing light 30 has reached the predetermined value. After evaluating the intensity of the rear surface outgoing light 31, the control and arithmetic device 260 turns off the semiconductor laser 10 at once.

Next, the control and arithmetic device 260 calculates the humidity on the basis of the intensity of the rear surface outgoing light 31 by referring to the above-described relation between the intensity of the rear surface outgoing light 31 and humidity (i.e., the relation between the intensity of the rear surface outgoing light 31 and humidity when the intensity of the front surface outgoing light 30 is the predetermined value).

According to the above-described two methods, the intensity of the rear surface outgoing light 31 is corrected on the basis of the intensity of the front surface outgoing light 30 that depends on only the factors other than the environmental parameter (humidity). Thus, the intensity of the rear surface outgoing light 31 is obtained as a value not depending on the factors (such as heat generation and deterioration of the semiconductor laser 10) other than the environmental parameter (humidity). As a result, the control and arithmetic device 260 can accurately calculate the environmental parameter on the basis of the intensity of the rear surface outgoing light 31 that depends on only the environmental parameter.

Embodiment 3

Still another embodiment of the present invention will be described below with reference to FIG. 4. For convenience of explanation, members having the same functions as those described in the above embodiments are denoted by the same reference sings, and description of those members is omitted.

In this embodiment, an optical sensor system 3 calculates a gas concentration as the environmental parameter. Stated in another way, in this embodiment, the gas concentration is a sensing target.

Figure 4:
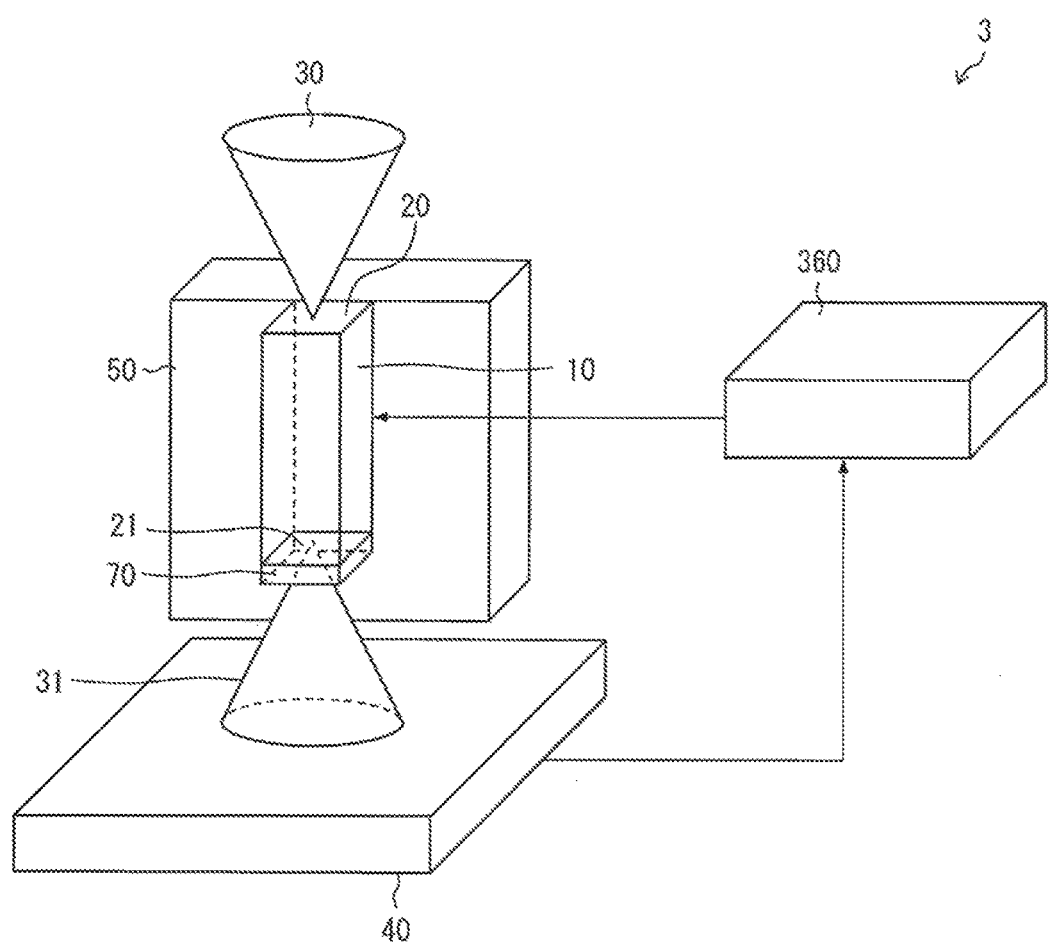
FIG. 4 is a schematic view illustrating a basic configuration of an optical sensor system according to Embodiment 3 of the present invention.

FIG. 4 is a schematic view illustrating a basic configuration of the optical sensor system 3 according to this embodiment. As illustrated in FIG. 4, the optical sensor system 3 includes the semiconductor laser 10, the photodiode 40, the sub-mount 50, a control and arithmetic device 360, and a gas sensitive film 70.

The gas sensitive film 70 is a thin film having an optical characteristic (refractive index or transmittance for laser light) that changes depending on the concentration of a specific kind of gas. As illustrated in FIG. 4, the gas sensitive film 70 is arranged on the rear surface 21 of the semiconductor laser 10. The refractive index or the transmittance of the gas sensitive film 70 changes depending on the concentration of the specific kind of gas. Therefore, the intensity of the rear surface outgoing light 31 transmitting through the gas sensitive film 70 increases or decreases depending on the concentration of the specific kind of gas.

The gas sensitive film 70 can be made of one of various polymer materials that expand (or swell) by absorbing, e.g., VOC (Volatile Organic Compounds) gas in air, thus causing changes in refractive indexes of those materials. Alternatively, the gas sensitive film 70 may be made of one of various oxide materials or catalyst materials that develop oxidation-reduction reactions or catalytic reactions with specific kinds of gases, thereby causing changes in refractive indexes or transmittances of those materials.

The material and the shape of the gas sensitive film 70 are not limited insofar as the intensity of the rear surface outgoing light 31 transmitting through the gas sensitive film 70 is changeable depending on the concentration of the specific kind of gas.

In order to suppress change in the intensity of the rear surface outgoing light 31 attributable to change in humidity, a moisture cutoff film for cutting off moisture is preferably disposed between the rear surface 21 and the gas sensitive film 70. The moisture cutoff film can be made of, e.g., a nitride thin film such as a SiN thin film or an AlN thin film.

The control and arithmetic device 360 controls the semiconductor laser 10. Furthermore, the control and arithmetic device 360 receives an electrical signal representing the intensity of the rear surface outgoing light 31 from the photodiode 40, and calculates the environmental parameter (gas concentration) from the received electrical signal. The control and arithmetic device 360 can be constituted by a plurality of chips and a microcomputer. A general-purpose arithmetic device, such as a personal computer, may be used as the control and arithmetic device 360. The control and arithmetic device 360 may calculate, by way of example, the humidity on the basis of a relation between gas concentration and light intensity, the relation being previously stored in a storage device (not illustrated).

With the configuration described above, the concentration of the specific kind of gas can be calculated as the environmental parameter.

Embodiment 4

Still another embodiment of the present invention will be described below with reference to FIGS. 5 and 6. For convenience of explanation, members having the same functions as those described in the above embodiment are denoted by the same reference sings, and description of those members is omitted.

The above Embodiments 1 to 3 have been described in connection with the examples in which one environmental parameter (humidity or gas concentration) is calculated. Embodiment 4 described here represents an example in which a plurality of environmental parameters (temperature and humidity) are calculated on the basis of an oscillation threshold and differential efficiency that are calculated from the intensity of the rear surface outgoing light 31. It is to be noted that an optical sensor system 1 according to this embodiment has the same configuration as that of the optical sensor system 1 (see FIG. 1) described in the above Embodiment 1.

[Oscillation Threshold 80 and Differential Efficiency 81]

First, the oscillation threshold 80 and the differential efficiency 81 are described with reference to FIG. 5. FIG. 5 is a graph depicting a light emission characteristic (i.e., a relation between injection current and light emission intensity) of a semiconductor laser as a reference. The semiconductor laser 10 incorporated in the optical sensor system 1 according to this embodiment also has a light emission characteristic similar to that of the semiconductor laser as the reference.

Figure 5:
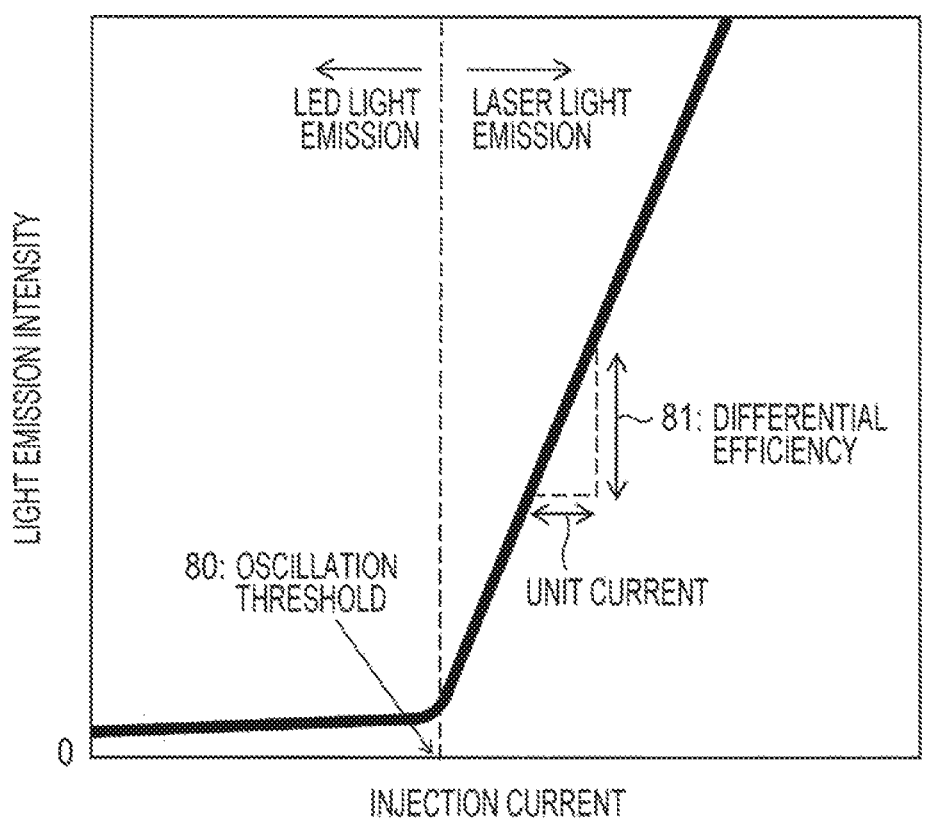
FIG. 5 is a graph depicting an oscillation characteristic of a typical semiconductor laser, the graph representing a relation between a current value of an injection current injected into the semiconductor laser and light emission intensity of the semiconductor laser.

As depicted in FIG. 5, the graph of the light emission characteristic of the semiconductor laser as the reference is generally divided into two regions with the oscillation threshold 80 being a boundary. When the injection current injected into the semiconductor laser is smaller than the oscillation threshold 80, photons are not amplified up to a sufficient number inside a resonator (waveguide and two mirrors) of the semiconductor laser, and laser oscillation does not occur. Therefore, laser light is not emitted from the semiconductor laser, and only light generated on the basis of the principle similar to that in generation of LED light is emitted. Thus, when the injection current is smaller than the oscillation threshold 80, the light emission intensity of the semiconductor laser is small.

On the other hand, when the injection current is larger than the oscillation threshold 80, photons are amplified up to a sufficient number inside the resonator, and laser oscillation occurs. As a result, laser light is emitted from the semiconductor laser. When the injection current is larger than the oscillation threshold 80, the light emission intensity of the semiconductor laser is large. When the injection current is larger than the oscillation threshold 80, the light emission intensity of the semiconductor laser is substantially proportional to the injection current. In other words, a relation between the light emission intensity of the semiconductor laser and the injection current can be expressed by a linear formula. In general, the intercept of a line expressed by the linear formula is defined as the oscillation threshold 80. A gradient (i.e., an increased amount of the light emission intensity per unit injection current) of the line expressed by the linear formula is called the differential efficiency 81.

[Method for Calculating Oscillation Threshold 80 and Differential Efficiency 81]

A method for calculating the oscillation threshold 80 and the differential efficiency 81 of the rear surface outgoing light 31 emitted from the semiconductor laser 10 are described here. The oscillation threshold 80 and the differential efficiency 81 are calculated by the control and arithmetic device 360. Instead of the control and arithmetic device 360, a user may calculate the oscillation threshold 80 and the differential efficiency 81.

First, the control and arithmetic device 360 injects a current having a current value (first current value), which is sufficiently larger than the oscillation threshold 80, into the semiconductor laser 10, thereby causing the semiconductor laser 10 to emit laser light.

After the intensity of the light emitted from the semiconductor laser 10 has been stabilized, the control and arithmetic device 360 evaluates the intensity (first intensity) of the rear surface outgoing light 31 on the basis of an electrical signal that has been received from the photodiode 40. A relation between the first intensity and the first current value is stored in a storage device (not illustrated). Immediately after evaluating the intensity of the rear surface outgoing light 31, the control and arithmetic device 360 turns off the semiconductor laser 10.

Next, the control and arithmetic device 360 injects a current having a current value (second current value), which is sufficiently larger than the oscillation threshold 80 and which is different from the first current value, into the semiconductor laser 10. After the intensity of the light emitted from the semiconductor laser 10 has been stabilized, the control and arithmetic device 360 evaluates the intensity (second intensity) of the rear surface outgoing light 31 on the basis of an electrical signal that has been received from the photodiode 40. A relation between the second intensity and the second current value is stored in the storage device.

By repeating the above-described operations, the control and arithmetic device 360 obtains a plurality of data representing a correspondence relation between the intensity of the rear surface outgoing light 31 (i.e., the first intensity, the second intensity, etc.) and the current value of the injection current injected into the semiconductor laser 10 (i.e., the first current value, the second current value, etc.). Then, the control and arithmetic device 360 executes a least square fitting process on the plurality of obtained data, and calculates a linear formula representing the relation between the intensity of the rear surface outgoing light 31 and the injection current injected into the semiconductor laser 10. An intercept of a line expressed by the calculated linear formula indicates the oscillation threshold 80, and a gradient of the line indicates the differential efficiency 81.

The above-described calculation method is one example. The control and arithmetic device 360 may calculate the oscillation threshold 80 and the differential efficiency 81 by another method.

By employing the oscillation threshold 80 and the differential efficiency 81 calculated as described above, the control and arithmetic device 360 calculates the environmental parameters (temperature and humidity) on the basis of the intensity of the rear surface outgoing light 31.

[Environmental Parameter Calculation Method 4]

The control and arithmetic device 360 calculates the environmental parameters (temperature and humidity) by the following method, for example.

Figure 6:
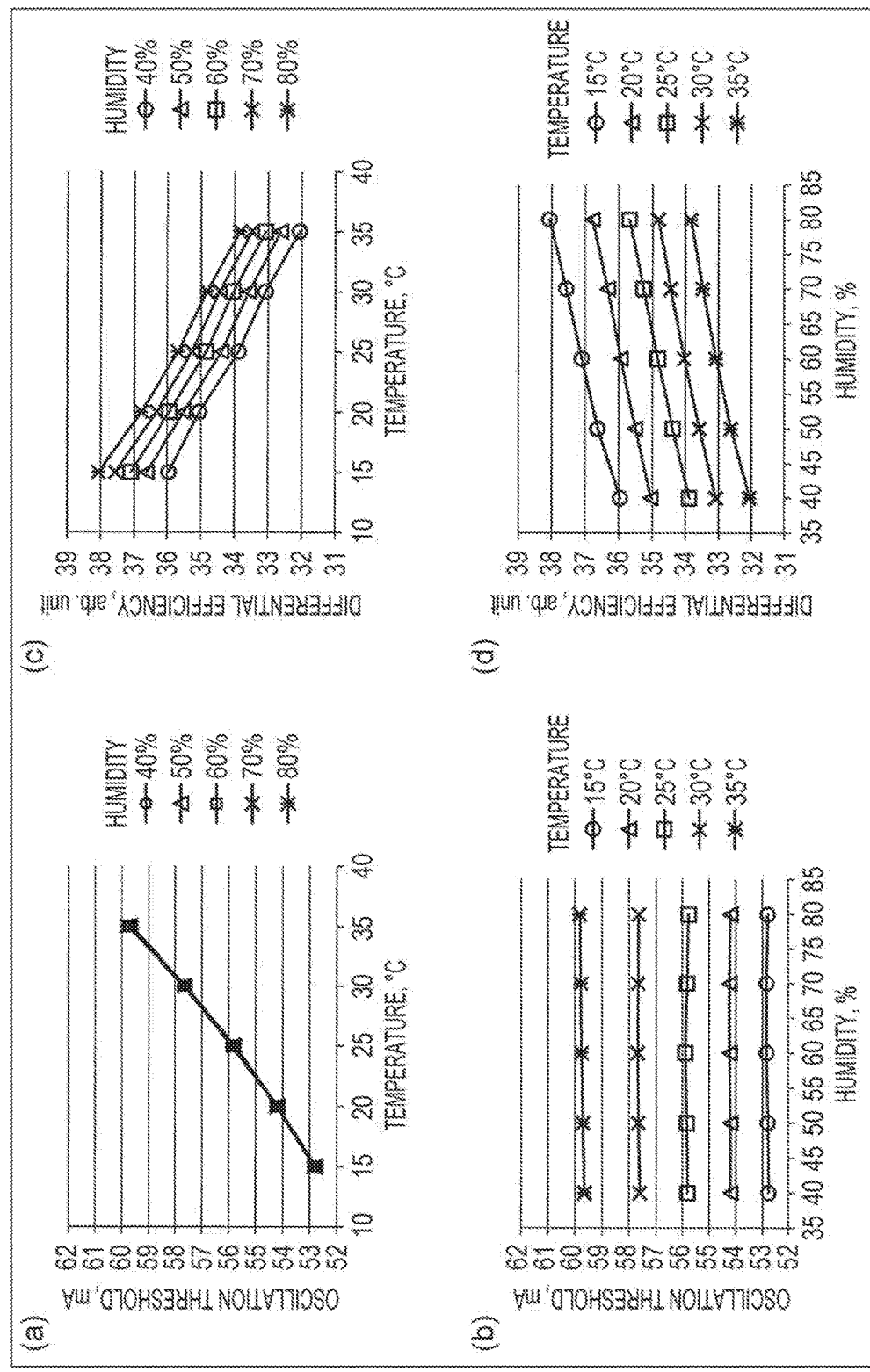
FIGS. 6(a) and 6(b) plot experimental data representing relations of an oscillation threshold of the rear surface outgoing light, which is emitted from a semiconductor laser included in the optical sensor system according to Embodiment 3 of the present invention, with respect to temperature and humidity, and FIGS. 6(c) and 6(d) plot experimental data representing relations of differential efficiency of the relevant rear surface outgoing light with respect to temperature and humidity.

FIGS. 6(*a*) to 6(*d*) plot experimental data representing temperature dependency and humidity dependency of the oscillation threshold 80 and the differential efficiency 81 of the rear surface outgoing light 31.

FIGS. 6(*a*) and 6(*b*) depict respectively the temperature dependency and the humidity dependency of the oscillation threshold 80. As depicted in FIG. 6(*a*), as the temperature rises, the oscillation threshold 80 increases monotonously. Moreover, as depicted in FIG. 6(*b*), the oscillation threshold 80 hardly depends on the humidity.

The control and arithmetic device 360 calculates the temperature on the basis of the temperature dependency, depicted in FIG. 6(*a*), of the oscillation threshold 80.

FIGS. 6(*c*) and 6(*d*) depict respectively the temperature dependency and the humidity dependency of the differential efficiency 81. As depicted in FIG. 6(*c*), as the temperature rises, the differential efficiency 81 decreases almost linearly. Moreover, as depicted in FIG. 6(*d*), as the humidity rises, the differential efficiency 81 increases almost linearly.

The control and arithmetic device 360 calculates the humidity on the basis of both the temperature previously calculated and the humidity dependency, depicted in FIG. 6(*d*) (or FIG. 6(*c*)), of the differential efficiency 81.

In calculating the humidity, the control and arithmetic device 360 may utilize a temperature detected by a temperature sensor (not illustrated) that is incorporated in the optical sensor system 1.

With the configuration described above, the control and arithmetic device 360 is able to calculate a plurality of environmental parameters (temperature and humidity). Therefore, the optical sensor system 1 including the control and arithmetic device 360 has a higher added value than the optical sensor system 1 of the above Embodiment 1, which includes the control and arithmetic device 60.

Embodiment 5

Still another embodiment of the present invention will be described below with reference to FIG. 7. For convenience of explanation, members having the same functions as those described in the above embodiments are denoted by the same reference sings, and description of those members is omitted.

In this embodiment, an optical gas sensor system 100 including the optical sensor system 1 according to the above Embodiment 1 is described. The optical gas sensor system 100 is an apparatus for sensing a concentration of a specific kind of gas. The optical gas sensor system 100 may include, instead of the optical sensor system 1, the optical sensor system 3 according to the above Embodiment 3.

Figure 7:
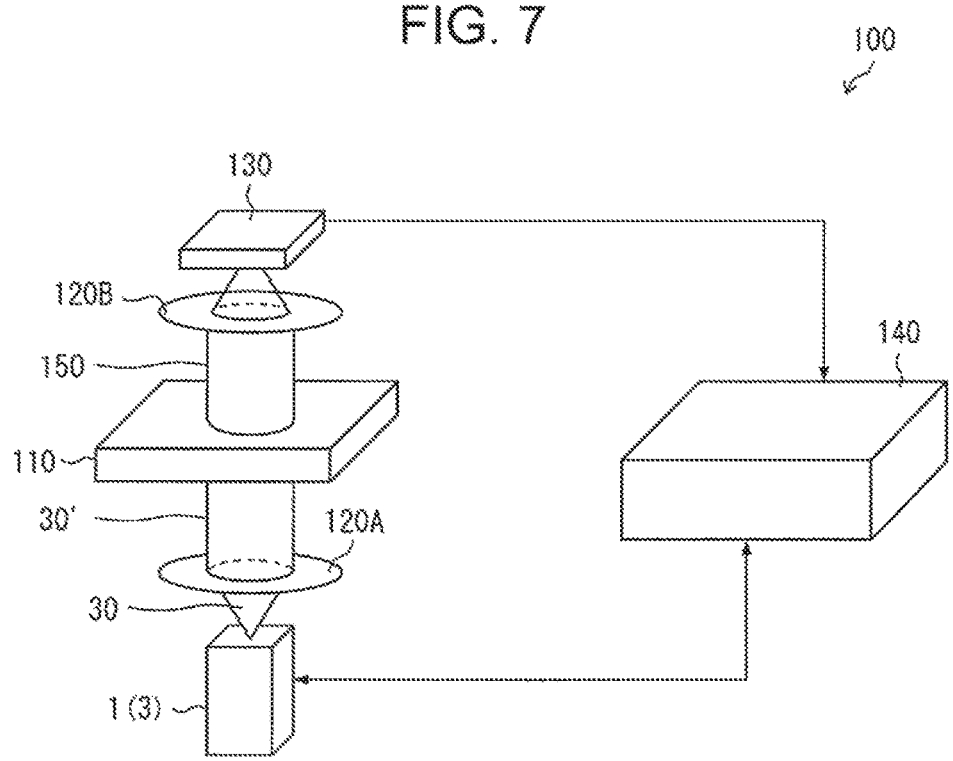
FIG. 7 is a schematic view illustrating a basic configuration of an optical gas sensor system according to Embodiment 5 of the present invention.

FIG. 7 is a schematic view illustrating a basic configuration of the optical gas sensor system 100 according to this embodiment. As illustrated in FIG. 7, the optical gas sensor system 100 includes the optical sensor system 1, a gas reactant 110, lenses 120A and 120B, a light detector 130 (transmitted light detector), and a control and arithmetic device 140 (gas detection unit).

The gas reactant 110 is a structure having an optical characteristic that changes depending on the concentration of the specific kind of gas present around the optical gas sensor system 100. The gas reactant 110 may be, e.g., a structure that changes its refractive index or transmittance depending on change in the gas concentration. As an alternative, the gas reactant 110 may be a structure that changes its reflectance or birefringence, or causes a wavelength shift of light (i.e., front surface outgoing light 30') incident on the gas reactant 110 depending on change in the gas concentration.

The gas reactant 110 can be made of one of various polymer materials that expand (or swell) by absorbing, e.g., VOC gas in air, thus causing changes in refractive indexes of those materials. Alternatively, the gas reactant 110 may be made of one of various oxide materials or catalyst materials that develop oxidation-reduction reactions or catalytic reactions with specific kinds of gases, thereby causing changes in refractive indexes or transmittances of those materials.

The material and the shape of the gas reactant 110 are not limited insofar as the intensity of the front surface outgoing light 30' transmitting through the gas reactant 110 is changeable depending on the concentration of the specific kind of gas.

The lens 120A collimates the front surface outgoing light 30 emitted from the optical sensor system 1. The front surface outgoing light 30' having been collimated by the lens 120A enters the gas reactant 110. The lens 120B condenses transmitted light 150, which has transmitted through the gas reactant 110, toward the light detector 130.

The light detector 130 is a device for detecting the transmitted light 150 that has been condensed by the lens 120B. Various photoelectric conversion devices, such as a photodiode and a CdS cell, can be optionally used as the light detector 130. The light detector 130 converts a detected value of the transmitted light 150 to an electrical signal (current signal or voltage signal), and sends the converted electrical signal to the control and arithmetic device 140.

The control and arithmetic device 140 controls the optical sensor system 1. Furthermore, the control and arithmetic device 140 calculates the concentration of the specific kind of gas on the basis of an electrical signal received from the light detector 130. The control and arithmetic device 140 can be constituted by a plurality of chips and a microcomputer. A general-purpose arithmetic device, such as a personal computer, may be used as the control and arithmetic device 140. Alternatively, the control and arithmetic device 140 may constitute one device together with the control and arithmetic device 60 in the optical sensor system 1. An operation of the control and arithmetic device 140 will be described below.

[Operation of Control and Arithmetic Device 140]

The control and arithmetic device 140 controls the optical sensor system 1, thereby causing the semiconductor laser 10 to emit light. As a result, the front surface outgoing light 30 is emitted from the optical sensor system 1. The front surface outgoing light 30 emitted from the optical sensor system 1 is collimated by the lens 120A and enters the gas reactant 110.

A part (transmitted light 150) of the front surface outgoing light 30' having entered the gas reactant 110 transmits through the gas reactant 110. Here, because the optical characteristic (refractive index or transmittance) of the gas reactant 110 changes depending on the concentration of the specific kind of gas, the intensity of the transmitted light 150 also changes depending on the concentration of the specific kind of gas. The transmitted light 150 is condensed by the lens 120B and is input to the light detector 130.

The light detector 130 detects the transmitted light 150 input thereto and converts a detected value of the transmitted light 150 to an electrical signal. The converted electrical signal is sent to the control and arithmetic device 140.

The control and arithmetic device 140 evaluates the intensity of the transmitted light 150 on the basis of the amplitude of the electrical signal received from the light detector 130. Then, the control and arithmetic device 140 calculates the concentration of the specific kind of gas on the basis of the evaluated intensity of the transmitted light 150 by referring to the relation between the intensity of the transmitted light 150 and the concentration of the specific kind of gas.

On the other hand, as described in the above Embodiment 1, the control and arithmetic device 60 in the optical sensor system 1 calculates at least one environmental parameter, e.g., the temperature, the humidity, or the gas concentration, from the intensity of the rear surface outgoing light 31. When the control and arithmetic device 60 calculates the gas concentration as in the above Embodiment 3, the gas to which the gas reactive film 70 (see FIG. 4) is reactive and the gas to which the gas reactant 110 is reactive may be different from each other.

When the gas reactant 110 has an optical characteristic that sensitively reacts to, e.g., temperature or humidity, the intensity of the transmitted light 150 detected by the light detector 130 changes depending on change in temperature or humidity. Thus, the intensity of the transmitted light 150 detected by the light detector 130 depends on not only gas concentration, but also temperature or humidity. Accordingly, an error (noise) generates in the gas concentration that is calculated on the basis of the intensity of the transmitted light 150.

In view of the above point, the control and arithmetic device 140 may correct, on the basis of the temperature or the humidity calculated by the optical sensor system 1, the gas concentration that has been calculated on the basis of the intensity of the transmitted light 150. With that feature, the control and arithmetic device 140 is able to calculate the gas concentration with higher accuracy. In the configuration described above, the relation between the gas concentration and the intensity of the transmitted light 150 when the temperature or the humidity is a predetermined value is determined in advance.

First, the control and arithmetic device 140 calculates a change amount of the intensity of the transmitted light 150 when the temperature or the humidity has changed from the predetermined value to a value of the temperature or the humidity calculated by the optical sensor system 1, while the gas concentration is kept at a constant value. The change amount of the intensity of the transmitted light 150 depends on the temperature or the humidity calculated by the optical sensor system 1.

Thereafter, the control and arithmetic device 140 subtracts the above-mentioned change amount from the intensity of the transmitted light 150, which has been detected by the light detector 130. The intensity of the transmitted light 150 after the subtraction depends on only the gas concentration.

Finally, the control and arithmetic device 140 calculates the gas concentration on the basis of the intensity of the transmitted light 150 after the subtraction by referring to the above-described relation (i.e., the relation between the gas concentration and the intensity of the transmitted light 150 when the temperature or the humidity is the predetermined value).

With the optical gas sensor system 100, as described above, it is possible to perform not only sensing of the concentration of the specific kind of gas, but also sensing of at least one environmental parameter, e.g., the temperature, the humidity, or the gas concentration, by the optical sensor system 1. In other words, the optical gas sensor system 100 is a multi-sensing device.

Accordingly, the optical gas sensor system 100 has a higher added value than an optical gas sensor system of related art, which can perform only sensing of the concentration of the specific kind of gas. Moreover, the number of parts in the optical gas sensor system 100 can be reduced in comparison with the optical gas sensor system of related art, which additionally requires a sensor for sensing the environmental parameter. Thus, the optical gas sensor system 100 can reduce the parts cost, the parts transport cost, and the parts assembly cost.

In another embodiment, the optical gas sensor system 100 may include, instead of the gas reactant 110, a sample holder allowing a desired sample to set thereon. The sample holder is arranged at the position of the gas reactant 110 in FIG. 7. In such a case, the optical gas sensor system 100 can be utilized as a transmittance measuring apparatus that measures the transmittance of the sample.

Embodiment 6

Still another embodiment of the present invention will be described below with reference to FIG. 8. For convenience of explanation, members having the same functions as those described in the above embodiments are denoted by the same reference sings, and description of those members is omitted.

In this embodiment, a particulate sensor system 200 including the optical sensor system 1 according to the above Embodiment 1 is described. The particulate sensor system 200 is an apparatus for detecting particulates (dust) floating in air. The particulate sensor system 200 may include, instead of the optical sensor system 1, the optical sensor system 3 according to the above Embodiment 3.

[Configuration of Particulate Sensor System 200]

Figure 8:
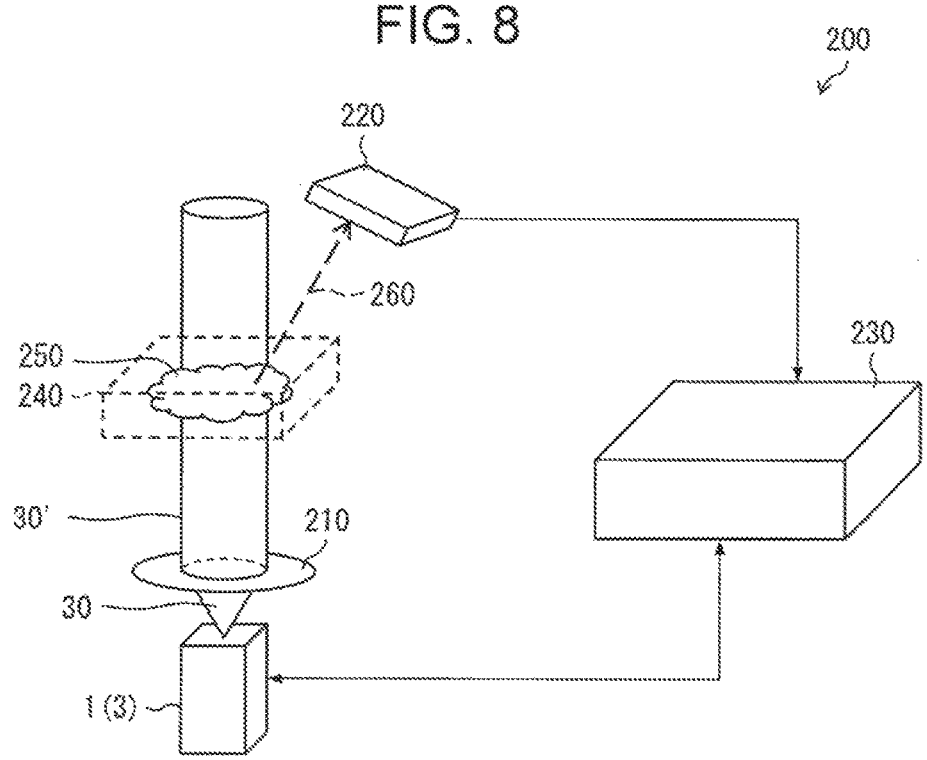
FIG. 8 is a schematic view illustrating a basic configuration of a particulate sensor system according to Embodiment 6 of the present invention.

FIG. 8 is a schematic view illustrating a basic configuration of the particulate sensor system 200 according to this embodiment. As illustrated in FIG. 8, the particulate sensor system 200 includes the optical sensor system 1, a lens 210, a light detector 220 (scattered light detector), and a control and arithmetic device 230 (particulate detection unit).

The lens 210 collimates the front surface outgoing light 30 that is emitted from the optical sensor system 1. The front surface outgoing light 30' collimated by the lens 210 enters a detection region 240.

When particulates 250 are floating in the detection region 240, a part of the front surface outgoing light 30' having entered the detection region 240 is scattered by the particulates 250, and scattered light 260 is generated. At least a part of the scattered light 260 thus generated is input to the light detector 220.

The light detector 220 detects the scattered light 260 input thereto. Furthermore, the light detector 220 converts a detected value of the scattered light 260 to an electrical signal (current signal or voltage signal), and sends the converted electrical signal to the control and arithmetic device 230. Various photoelectric conversion devices, such as a photodiode and a CdS cell, can be optionally used as the light detector 220.

The control and arithmetic device 230 controls the optical sensor system 1. Furthermore, the control and arithmetic device 230 evaluates the intensity of the scattered light 260 on the basis of the amplitude of the electrical signal received from the light detector 220. The control and arithmetic device 230 then determines, on the basis of the evaluated intensity of the scattered light 260, whether the particulates 250 are present in the detection region 240. For example, when the intensity of the scattered light 260 is not less than a predetermined value, the control and arithmetic device 230 may determine that the particulates 250 are present in the detection region 240.

When the particulates 250 are present in the detection region 240, the control and arithmetic device 230 calculates (evaluates) the content of the particulates 250 present in the detection region 240 on the basis of the intensity of the scattered light 260.

The control and arithmetic device 230 can be constituted by a plurality of chips and a microcomputer. A general-purpose arithmetic device, such as a personal computer, may be used as the control and arithmetic device 230. Alternatively, the control and arithmetic device 230 may constitute one device together with the control and arithmetic device 60 in the optical sensor system 1.

As described in the above Embodiment 1, the control and arithmetic device 60 in the optical sensor system 1 calculates at least one environmental parameter, e.g., the temperature, the humidity, or the gas concentration, on the basis of the intensity of the rear surface outgoing light 31. When the control and arithmetic device 60 causes the semiconductor laser 10 to emit the light in order to calculate the environmental parameter, a part or the whole of the emitted light enters, as the front surface outgoing light 30', the detection region 240.

When evaluating the content of the particulates 250 in the detection region 240, the control and arithmetic device 230 preferably utilizes the above-mentioned front surface outgoing light 30' (i.e., the front surface outgoing light 30' that enters the detection region 240 when the control and arithmetic device 60 causes the semiconductor laser 10 to emit the light in order to calculate the environmental parameter). With that configuration, while the semiconductor laser 10 is operated to emit the light once, the environmental parameter is calculated by the control and arithmetic device 60, and the content of the particulates 250 in the detection region 240 is evaluated by the control and arithmetic device 230.

Therefore, the control and arithmetic device 60 and the control and arithmetic device 230 are not required to cause the semiconductor laser 10 to emit the light two or more times. Furthermore, an accumulated light emission time of the semiconductor laser 10 is shortened. As a result, the lifetimes of the semiconductor laser 10, the optical sensor system 1, and the particulate sensor system 200 are prolonged. In addition, the power consumption of the particulate sensor system 200 is reduced.

With the particulate sensor system 200, as described above, it is possible not only to detect particulates floating in air (i.e., in the detection region 240), but also to calculate at least one environmental parameter, e.g., the temperature, the humidity, or the gas concentration, by the optical sensor system 1. In other words, the particulate sensor system 200 is a multi-sensing device capable of sensing a plurality of targets related to quality and stability of air.

Accordingly, the particulate sensor system 200 has a higher added value than a particulate sensor system of related art, which can detect only particulates floating in air. Moreover, since the particulate sensor system 200 is not required to additionally include a sensor for sensing the environmental parameter, the number of parts can be reduced in comparison with the particulate sensor system of related art. As a result, the particulate sensor system 200 can reduce the parts cost, the parts transport cost, and the parts assembly cost.

In another embodiment, the particulate sensor system 200 may include, in the detection region 240, a sample holder allowing a desired sample to set thereon. In such a case, the particulate sensor system 200 can be utilized as a transmittance measuring apparatus that measures the transmittance of the sample set on the sample holder.

[Configuration of Air Cleaner 201]

Figure 9:
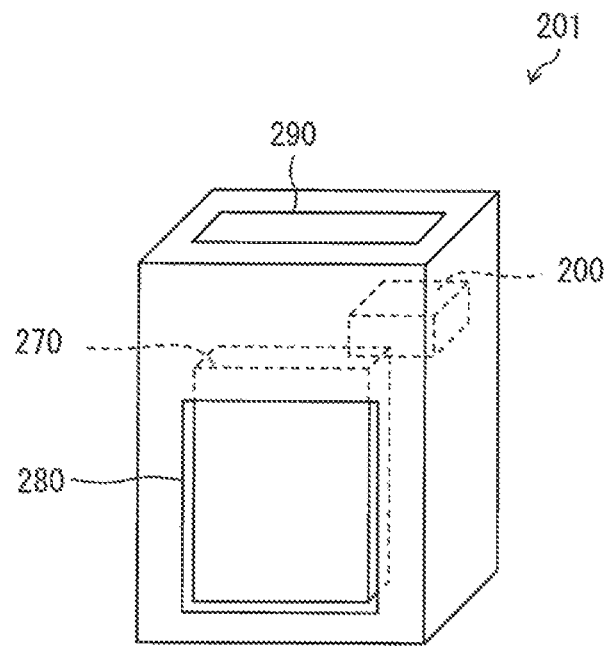
FIG. 9 is a schematic view illustrating a basic configuration of an air cleaner including the particulate sensor system according to Embodiment 6 of the present invention.

One example of an air cleaner 201 including the above particulate sensor system 200 will be described below with reference to FIG. 9. FIG. 9 is a schematic view illustrating a basic configuration of the air cleaner 201.

As illustrated in FIG. 9, the air cleaner 201 includes the particulate sensor system 200, an air cleaning filter 270, an air intake opening 280, and an air blowout opening 290.

The air cleaning filter 270 removes contaminants, such as particulates and gases, contained in air flowing into the air cleaner 201 through the air intake opening 280. The air cleaning filter 270 may be, e.g., a HEPA filter (High Efficiency Particulate Air Filter). The air cleaning filter 270 may jet the air, which has flowed into the air cleaner 201, toward water, or may cause the air to move under water for the purpose of cleaning the relevant air. The air having been cleaned after passing through the air cleaning filter 270 is delivered to the air blowout opening 290.

The air intake opening 280 takes in ambient air into the air cleaner 201, and supplies the taken-in air to the air cleaning filter 270.

Air from which the contaminants have been removed after passing through the air cleaning filter 270 is blown out to the exterior of the air cleaner 201 through the air blowout opening 290.

The air cleaner 201 may have the humidifying function or the dehumidifying function. In such a case, the air cleaner 201 may control a level of humidification performance or dehumidification performance on the basis of humidity (environmental parameter) that is calculated by the optical sensor system 1 incorporated in the particulate sensor system 200.

Furthermore, the air cleaner 201 may control a level of air cleaning performance on the basis of the amount of particulates detected by the particulate sensor system 200. Alternatively, the air cleaner 201 may notify the state and safety of air to a user by displaying, on a display unit (not illustrated), the amount of particulates detected by the particulate sensor system 200 or the environmental parameter calculated by the optical sensor system 1.

In any of the above-described configurations, the air cleaner 201 is operated on the basis of only the result of sensing by the particulate sensor system 200 or by the optical sensor system 1. Thus, the particulate sensor system 200 is not required to include a plurality of sensors in order to implement the above-described operation. Accordingly, the particulate sensor system 200 can reduce, in addition to the number of parts, the parts cost, the parts transport cost, and the parts assembly cost in comparison with a particulate sensor system of related art, which includes a plurality of sensors.

Embodiment 7

Still another embodiment of the present invention will be described below with reference to FIG. 10. For convenience of explanation, members having the same functions as those described in the above embodiments are denoted by the same reference sings, and description of those members is omitted.

In this embodiment, a light emitting apparatus 300 including the optical sensor system 1 according to the above Embodiment 1 is described. The light emitting apparatus 300 is an apparatus for emitting the laser light, which has been generated by the semiconductor laser 10 incorporated in the optical sensor system 1, to the exterior. The light emitting apparatus 300 controls light emission conditions of the semiconductor laser 10 on the basis of the result of the environmental parameter calculated by the optical sensor system 1. The light emitting apparatus 300 may include, instead of the optical sensor system 1, the optical sensor system 3 according to the above Embodiment 3.

Figure 10:
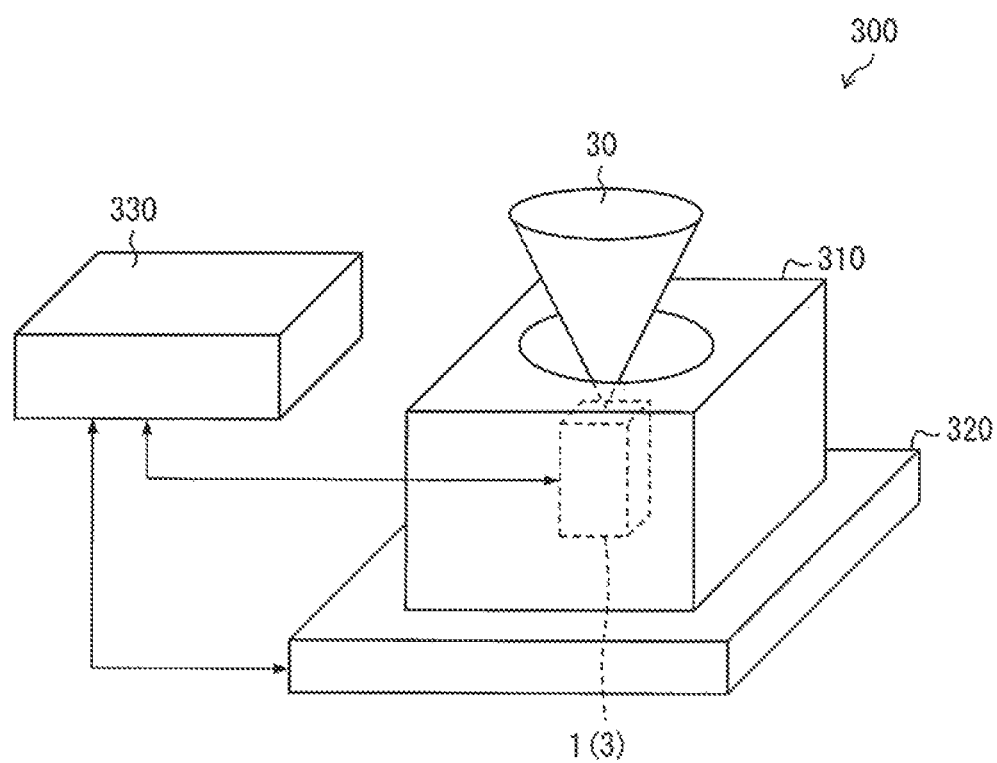
FIG. 10 is a schematic view illustrating a basic configuration of a light emitting apparatus according to Embodiment 7 of the present invention.

FIG. 10 is a schematic view illustrating a basic configuration of the light emitting apparatus 300 according to this embodiment. As illustrated in FIG. 10, the light emitting apparatus 300 includes the optical sensor system 1, a case 310, a temperature regulator 320, and a control and arithmetic device 330 (light-emission condition control unit).

The optical sensor system 1 calculates at least one environmental parameter (temperature, humidity, or gas concentration) and sends the calculated environmental parameter to the control and arithmetic device 330.

The case 310 protects the entirety of the optical sensor system 1. The case 310 protects particularly the semiconductor laser 10 that is incorporated in the optical sensor system 1. The case 310 is generally made of resin, metal, or glass, for example. The case 310 has a window through which the front surface outgoing light 30 emitted from the semiconductor laser 10 is led out to the exterior of the case 310. The front surface outgoing light 30 led out to the exterior is utilized in various application fields.

The semiconductor laser 10 is classified into the type used in a state opened to the atmospheric air, and the type used in a state sealed in pure nitrogen or pure air containing no humidity. When the semiconductor laser 10 is of the type used in the state opened to the atmospheric air, the case 310 is not required to be sealed off. Thus, in that situation, the interior of the case 310 is opened to the atmospheric air.

On the other hand, when the semiconductor laser 10 is of the type used in the sealed state, the case 310 is closely sealed off. In that situation, the interior of the case 310 is filled with pure nitrogen or pure air.

The temperature regulator 320 regulates a temperature of the optical sensor system 1 such that the temperature of the optical sensor system 1 is kept at a preset temperature. Furthermore, the temperature regulator 320 expels out heat generated from the optical sensor system 1 to the exterior. The preset temperature of the optical sensor system 1 may be set by the user or the control and arithmetic device 330. The temperature regulator 320 may be constituted by, e.g., a Peltier element or a fin. When the temperature regulator 320 is constituted by a Peltier element, the temperature of the optical sensor system 1 can be exactly controlled. The temperature regulator 320 can cool the temperature of the optical sensor system 1 down to a level not higher than an environmental temperature. When the temperature of the optical sensor system 1 is cooled down to the level not higher than the environmental temperature, there is a possibility that dew condensation occurs in the optical sensor system 1.

The control and arithmetic device 330 controls the optical sensor system 1. Furthermore, the control and arithmetic device 330 controls the preset temperature of the temperature regulator 320 and the light emission conditions of the semiconductor laser 10 on the basis of the environmental parameter (ambient parameter) received from the optical sensor system 1. The control and arithmetic device 330 can be constituted by a plurality of chips and a microcomputer. A general-purpose arithmetic device, such as a personal computer, may be used as the control and arithmetic device 330. Alternatively, the control and arithmetic device 330 may constitute one device together with the control and arithmetic device 60 in the optical sensor system 1.

Usually, the semiconductor laser 10 is not manufactured on the assumption that it is used under an environment at high humidity. Therefore, when the semiconductor laser 10 is used under the environment at high humidity, a failure occurs with a very high possibility. Moreover, when the temperature of the optical sensor system 1 drops below the dew point, there is a possibility that dew condensation occurs in the optical sensor system 1. In the case where the dew condensation has occurred in the optical sensor system 1 and water droplets have adhered to the semiconductor laser 10, those water droplets may cause a failure of the semiconductor laser 10. The control and arithmetic device 330 operates in a way of solving the above problem. The operation of the control and arithmetic device 330 will be described below.

[Operation of Control and Arithmetic Device 330]

The operation of the control and arithmetic device 330 is different depending on the type of the semiconductor laser 10, and on whether the case 310 is sealed off or not. More specifically, the operation of the control and arithmetic device 330 is different between the case (1) where the semiconductor laser 10 is of the type used in the state sealed in pure nitride air or pure air and where the case 310 is sealed off, and the case (2) where the semiconductor laser 10 is of the type used in the state opened to the atmospheric air and where the case 310 is not sealed off.

(Operation of Control and Arithmetic Device 330 in Case (1))

The operation of the control and arithmetic device 330 in the above case (1) is first described. In this situation, the control and arithmetic device 330 determines, on the basis of a level of the humidity detected by the optical sensor system 1, whether the sealing-off of the case 310 is broken or not. Moreover, when the humidity calculated by the optical sensor system 1 is larger than a predetermined upper limit value, the light emission of the semiconductor laser 10 is stopped. The operation of the control and arithmetic device 330 is described in more detail below.

The control and arithmetic device 330 controls the optical sensor system 1, thereby causing the semiconductor laser 10 to emit light. While the control and arithmetic device 330 operates the semiconductor laser 10 to emit the light, the optical sensor system 1 detects the humidity (environmental parameter) around the optical sensor system 1. The optical sensor system 1 notifies the detected humidity to the control and arithmetic device 330.

When the sealing-off of the case 310 is not broken, the interior of the case 310 is kept in a state of low humidity. On the other hand, when the sealing-off of the case 310 is broken, moisture in the atmospheric air (outside the case 310) flows into the case 310. Accordingly, when the sealing-off of the case 310 is broken, the humidity detected by the optical sensor system 1 is relatively high.

When the humidity notified from the optical sensor system 1 is hot higher than the predetermined upper limit value, the control and arithmetic device 330 continues the light emission of the semiconductor laser 10. On the other hand, when the humidity notified from the optical sensor system 1 is higher than the predetermined upper limit value, the control and arithmetic device 330 stops the light emission of the semiconductor laser 10.

Thus, the control and arithmetic device 330 can prevent the semiconductor laser 10 from continuing the light emission in the environment at the high humidity. As a result, a possibility of a failure of the semiconductor laser 10 is reduced.

The light emitting apparatus 300 may include a display device and may operate the display device to display information indicating that the sealing-off of the case 310 is broken. With such a configuration, the light emitting apparatus 300 can prompt the user to seal off the case 310 again, and to replace individual parts of the case 310.

(Operation of Control and Arithmetic Device 330 in Case (2))

Next, the operation of the control and arithmetic device 330 in the above case (2) is described. In this situation, the control and arithmetic device 330 prevents the occurrence of dew condensation in the optical sensor system 1. The operation of the control and arithmetic device 330 is described in more detail below. It is here assumed that the temperature regulator 320 is constituted by a Peltier element.

The control and arithmetic device 330 controls the optical sensor system 1, thereby causing the semiconductor laser 10 to emit light. While the control and arithmetic device 330 operates the semiconductor laser 10 to emit the light, the optical sensor system 1 detects the humidity (environmental parameter) around the optical sensor system 1 by employing the rear surface outgoing light 31. The optical sensor system 1 notifies the detected humidity to the control and arithmetic device 330.

On the basis of the humidity notified from the optical sensor system 1 and the preset temperature of the temperature regulator 320, the control and arithmetic device 330 calculates a temperature (dew point) at which the dew condensation occurs in the optical sensor system 1. When the preset temperature of the temperature regulator 320 is higher than the dew point, the control and arithmetic device 330 continues the light emission of the semiconductor laser 10. On the other hand, the preset temperature of the temperature regulator 320 is lower than the dew point, the control and arithmetic device 330 stops the light emission of the semiconductor laser 10.

Thus, the control and arithmetic device 330 can prevent the occurrence of the dew condensation in the optical sensor system 1. As a result, a possibility of a failure of the semiconductor laser 10 is reduced.

Alternatively, when the preset temperature of the temperature regulator 320 is lower than the dew point, the control and arithmetic device 330 may raise the preset temperature of the temperature regulator 320. As a result, the temperature of the optical sensor system 1 rises. Hence the dew condensation becomes hard to occur in the optical sensor system 1.

As described above, the light emitting apparatus 300 controls the light emission conditions of the semiconductor laser 10 on the basis of the result of the environmental parameter calculated by the optical sensor system 1. It is hence possible to prevent not only a failure of the semiconductor laser 10, but also the occurrence of dew condensation in the optical sensor system 1.

Furthermore, the light emitting apparatus 300 is not required to include a humidity sensor for detecting humidity. Accordingly, the light emitting apparatus 300 can reduce, in addition to the number of parts, the parts cost, the parts transport cost, and the parts assembly cost in comparison with a light emitting apparatus of related art, which includes the humidity sensor.

The optical sensor system 1 may detect, as the environmental parameter, a gas concentration of corrosive gas (e.g., ozone or chlorine), which may cause a failure of the semiconductor laser 10, instead of humidity. In such a case, the control and arithmetic device 330 controls the light emission conditions of the semiconductor laser 10 on the basis of a level of the gas concentration of the corrosive gas detected by the optical sensor system 1.

Embodiment 8

Still another embodiment of the present invention will be described below with reference to FIG. 11. For convenience of explanation, members having the same functions as those described in the above embodiments are denoted by the same reference sings, and description of those members is omitted.

In this embodiment, an image printing apparatus 400 including the optical sensor system 1 according to the above Embodiment 1 is described. The image printing apparatus 400 is an apparatus with the image printing function of printing an image on a sheet of print paper P. The image printing apparatus 400 controls printing conditions of an image on the basis of the environmental parameter calculated by the optical sensor system 1. Here, the term "printing conditions" imply conditions that specify an operation or a state of the image printing apparatus 400 in a process of printing an image. Specific examples of the printing conditions are described later. The image printing apparatus 400 may include, instead of the optical sensor system 1, the optical sensor system 3 according to the above Embodiment 3.

Figure 11:
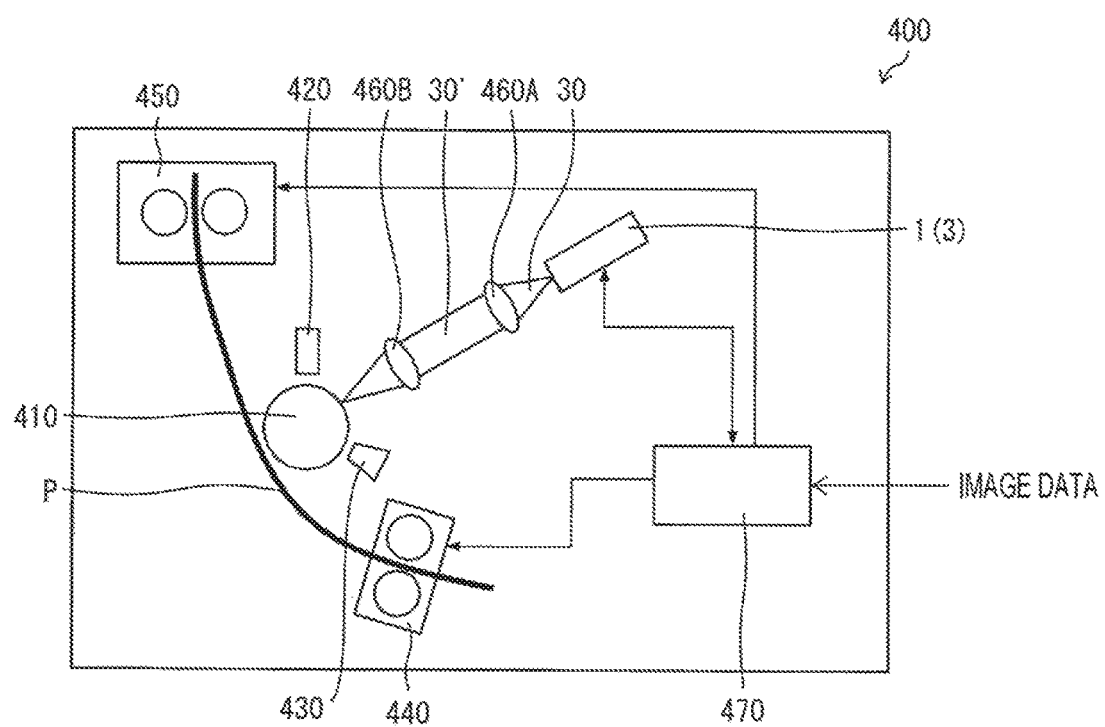
FIG. 11 is a schematic view illustrating a basic configuration of an image printing apparatus according to Embodiment 8 of the present invention.

FIG. 11 is a schematic view illustrating a basic configuration of the image printing apparatus 400 according to this embodiment. As illustrated in FIG. 11, the image printing apparatus 400 includes the optical sensor system 1, a photoconductive drum 410, a charging unit 420, a toner unit 430, a paper feed unit 440, a fusing unit 450, lenses 460A and 460B, and a control and arithmetic device 470 (condition control unit).

The optical sensor system 1 calculates, as described in the above Embodiment 4, a plurality of environmental parameters (such as temperature and humidity) on the basis of the relation between the current value of the injection current injected into the semiconductor laser 10 and the intensity of the rear surface outgoing light 31.

A charged photosensitive sheet is pasted to a surface of the photoconductive drum 410. Charges on the charged photosensitive sheet are removed upon irradiation with the front surface outgoing light 30' from the optical sensor system 1. The photosensitive sheet is made of a material (e.g., an organic photo conductor (OPC) or selenium) of which electrical conductivity changes upon irradiation with light. When the photosensitive sheet on the photoconductive drum 410 is irradiated with the front surface outgoing light 30', electrical conductivity of the photosensitive sheet is increased. With an increase of the electrical conductivity, the charges accumulated on the surface of the photosensitive sheet are moved to flow out of the photosensitive sheet. A region of the photosensitive sheet where the sheet surface has not been irradiated with the light is kept in a charged state, while a region of the photosensitive sheet where the sheet surface has been irradiated with the light changes to a non-charged state. As a result, an electrostatic latent image drawn with charges is formed in the region of the photosensitive sheet where the sheet surface has not been irradiated with the light.

The charging unit 420 charges the photosensitive sheet pasted to the surface of the photoconductive drum 410. In general, a corona discharge method is utilized to charge the photosensitive sheet. In the case of utilizing the corona discharge method, the charging unit 420 applies a high voltage to a needle electrode, thereby causing corona discharge and generating charges to be attached to the photosensitive sheet.

The toner unit 430 develops the electrostatic latent image that has been formed over the photosensitive sheet on the photoconductive drum 410. In general, a magnetic brush development method is utilized to develop the electrostatic latent image. In the case of utilizing the magnetic brush development method, the toner unit 430 operates as follows. Toner particles and magnetic powder (carriers) are mixed to make the toner particles attached to the carriers. Thereafter, the carriers to which the toner particles have been attached are raised into a brush-like shape with the aid of magnetic force. The brush-shaped carriers are then rubbed against the photosensitive sheet on the photoconductive drum 410. With such a rubbing operation, the toner particles attached to the carriers are coupled to the charges constituting the electrostatic latent image that has been formed over the photosensitive sheet. As a result, the electrostatic latent image is developed.

The paper feed unit 440 includes two rollers and rotates those rollers to feed the print paper P, which is sandwiched between the rollers, toward the photoconductive drum 410. The print paper P fed toward the photoconductive drum 410 from the paper feed unit 440 is brought into contact with the photosensitive sheet on the photoconductive drum 410. At that timing, the toner particles attached to the photosensitive sheet on the photoconductive drum 410 are moved onto the print paper P. As a result, an image (developed electrostatic latent image) drawn over the photosensitive sheet on the photoconductive drum 410 is transferred to the print paper P.

The fusing unit 450 includes a roller and a heater. The fusing unit 450 fixes (fuses) the toner particles onto the print paper by heating the print paper P with the heater while the print paper P is held against the heater by the roller.

The lens 460A collimates the front surface outgoing light 30 emitted from the optical sensor system 1. The lens 460B condenses the front surface outgoing light 30' that has been collimated by the lens 460A. The front surface outgoing light 30' condensed by the lens 460B is applied to the photosensitive sheet on the photoconductive drum 410.

The control and arithmetic device 470 controls the individual units and the optical sensor system 1 in the image printing apparatus 400. Furthermore, the control and arithmetic device 470 processes image data received from the exterior, and receives the environmental parameter from the optical sensor system 1. The control and arithmetic device 470 can be constituted by a plurality of chips and a microcomputer. A general-purpose arithmetic device, such as a personal computer, may be used as the control and arithmetic device 470. Alternatively, the control and arithmetic device 470 may constitute one device together with the control and arithmetic device 60 in the optical sensor system 1.

[Operation of Control and Arithmetic Device 470]

When the control and arithmetic device 470 receives image data from the exterior, it prints an image on the print paper P in accordance with the following procedures.

First, the control and arithmetic device 470 controls the paper feed unit 440 to feed the print paper P toward the photoconductive drum 410. Furthermore, the control and arithmetic device 470 controls the charging unit 420 to charges the photosensitive sheet on the photoconductive drum 410.

Subsequently, the control and arithmetic device 470 controls the optical sensor system 1 to emit the front surface outgoing light 30. At that time, the control and arithmetic device 470 draws the electrostatic latent image over the photosensitive sheet on the photoconductive drum 410 by controlling a direction of emission of the front surface outgoing light 30 in accordance with the received image data.

Thereafter, the control and arithmetic device 470 controls the toner unit 430 to develop the electrostatic latent image that has been drawn over the photosensitive sheet on the photoconductive drum 410. Upon the print paper P, which is fed by the paper feed unit 440, contacting the photoconductive drum 410, the image drawn over the photosensitive sheet on the photoconductive drum 410 is transferred to the print paper P. Finally, the control and arithmetic device 470 controls the fusing unit 450 such that the image having been transferred to the print paper P is fixedly fused to the print paper P.

In the above-described procedures, the control and arithmetic device 470 can adjust printing conditions on the basis of at least one environmental parameter (e.g., temperature or humidity) that has been calculated by the optical sensor system 1.

For example, an optimum amount of light exposed to the organic photo conductor or selenium, which is used as the material of the photosensitive sheet on the photoconductive drum 410, is different depending on temperature and humidity. In view of such a point, the control and arithmetic device 470 may adjust the amount of light exposed to the photosensitive sheet on the basis of at least one of the temperature and the humidity calculated by the optical sensor system 1.

Additionally, the control and arithmetic device 470 may further adjust various printing conditions on the basis of the environmental parameter(s) calculated by the optical sensor system 1. The printing conditions adjustable by the control and arithmetic device 470 include (1) an amount of charges charged over the photosensitive sheet on the photoconductive drum 410, (2) an image heating temperature when the image having been transferred to the print paper P from the photosensitive sheet is fixedly fused to the print paper P, and (3) a rotating speed of each of the rollers in the image printing apparatus 400.

As a result, the control and arithmetic device 470 can improve quality of the printing and can reduce a possibility of the occurrence of a trouble, such as paper jamming.

The image printing apparatus 400 is not required to include a sensor for detecting the environmental parameter (e.g., temperature or humidity). Accordingly, the image printing apparatus 400 can reduce, in addition to the number of parts, the parts cost, the parts transport cost, and the parts assembly cost in comparison with an image printing apparatus provided of related art, which includes the sensor for detecting the environmental parameter (e.g., temperature or humidity).

The control and arithmetic device 470 may be constituted to be able to adjust an image printing density. The image printing density changes depending on the amount of light exposed to the photosensitive sheet on the photoconductive drum 410. When the semiconductor laser 10 is driven in accordance with the Pulse Amplitude Modulation (PWM) method, the control and arithmetic device 470 can simply adjust the amount of light exposed to the photosensitive sheet on the photoconductive drum 410 by controlling the arithmetic device 60 so as to adjust a pulse width of the front surface outgoing light 30 while a constant amount of the injection current is injected into the semiconductor laser 10.

For that reason, from the viewpoint of practical use of the front surface outgoing light 30, the laser light emitted from the semiconductor laser 10 is preferably subjected to the Pulse Amplitude Modulation.

However, when the control and arithmetic device 470 drives the semiconductor laser 10 with the constant amount of the injection current by employing the Pulse Amplitude Modulation method, the control and arithmetic device 60 cannot determine the relation between the injection current injected into the semiconductor laser 10 and the intensity of the rear surface outgoing light 31.

For that reason, from the viewpoint of use of the rear surface outgoing light 31 (i.e., from the viewpoint of calculating the environmental parameter), it is preferable that the laser light emitted from the semiconductor laser 10 is not subjected to the Pulse Amplitude Modulation (namely, that the semiconductor laser 10 emits an analog wave).

Thus, when an optimum driving method of the semiconductor laser 10 is different between the use of the front surface outgoing light 30 and the use of the rear surface outgoing light 31, the optimum driving method is preferably selected depending on the use of each of those lights. More specifically, when the control and arithmetic device 470 performs exposure to the photosensitive sheet on the photoconductive drum 410 by employing the front surface outgoing light 30, the control and arithmetic device 60 drives the semiconductor laser 10 in accordance with the Pulse Amplitude Modulation method. On the other hand, when the control and arithmetic device 60 calculates the environmental parameter by employing the rear surface outgoing light 31, the control and arithmetic device 60 drives the semiconductor laser 10 in accordance with the analog modulation method.

Moreover, when optimum light emission conditions for the semiconductor laser 10 are different between the use of the front surface outgoing light 30 and the use of the rear surface outgoing light 31, the optimum light emission conditions are preferably selected depending on the use of each of those lights. Here, the light emission conditions include various factors affecting an output power of light generated from a light emitting device. Optionally selectable examples of the light emission conditions include a control temperature, an injection current value, a driving mode (such as continuous oscillation or pulsed oscillation), and a modulation mode (such as analog modulation, PWM modulation, or PAM modulation).

[Recapitulation]

A first aspect of the present invention provides an optical sensor system (1 to 3) including a light emitting device (semiconductor laser 10) that generates first emission light (front surface outgoing light 30) for use in a predetermined application, the light emitting device further generating second emission light (rear surface outgoing light 31), wherein the optical sensor system further includes an emission light detector (photodiode 40) that detects the second emission light, and an environmental parameter calculation unit (control and arithmetic device 60) that calculates an environmental parameter, as an index of an environment around the light emitting device, by employing a value of the second emission light detected by the emission light detector.

With the features described above, the environmental parameter is calculated from the value of the second emission light detected by the emission light detector. Thus, since the optical sensor system is not required to additionally include a sensor for detecting the environmental parameter, reduction in size and cost of the optical sensor system can be realized. The environmental parameter may be at least one of temperature, humidity, and gas concentration. The calculated environmental parameter can be utilized in various operations of the optical sensor system.

On the other hand, the first emission light output from the optical sensor system is used in various applications other than the calculation of the environmental parameter. Accordingly, the optical sensor system can be provided in which the first emission light can be used as an ordinary light source, and in which the environmental parameter can be calculated by employing the second emission light.

According to a second aspect of the present invention, in the optical sensor system according to the first aspect, assuming that a factor affecting an output power of the emission light generated by the light emitting device is called a light emission condition, the light emission condition of the light emitting device when the environmental parameter calculation unit calculates the environmental parameter may be different from the light emission condition when the first emission light output to the exterior is used in the predetermined application.

With the feature described above, an optimum light emission condition of the light emitting device can be selected for each of the case where the environmental parameter is calculated, and the case where the first emission light is used in the predetermined application. The light emitting device may be a semiconductor laser. Since the semiconductor laser has a small size and is inexpensive, it is suitable as a light source in the optical sensor system according to the present invention.

According to a third aspect of the present invention, in the optical sensor system according to the first aspect, at least a part of the emission light generated from the light emitting device when the environmental parameter calculation unit calculates the environmental parameter may be utilized as the first emission light in the predetermined application.

With the feature described above, while the light emitting device is operated to emit the light once, the environmental parameter can be calculated by employing the second emission light, and the first emission light can be used in the predetermined application. In comparison with the case of operating the light emitting device to emit the light several times, therefore, an accumulated light emission time of the light emitting device can be shortened and the lifetime of the optical sensor system can be prolonged. In addition, the power consumption of the optical sensor system can be reduced.

According to a fourth aspect of the present invention, in the optical sensor system according to any one of the first to third aspects, the environmental parameter calculation unit may calculate the plurality of environmental parameters.

With the feature described above, since the plurality of environmental parameters can be calculated, an added value of the optical sensor system can be increased in comparison with the case of calculating one environmental parameter.

According to a fifth aspect of the present invention, in the optical sensor system according to any one of the first to fourth aspects, the environmental parameter calculation unit may calculate the environmental parameter on the basis of the value of the second emission light detected by the emission light detector when a constant amount of current is injected into the light emitting device.

With the feature described above, the environmental parameter is calculated on the basis of the intensity of the second emission light emitted from the light emitting device to which the constant amount of current is injected. Accordingly, the optical sensor system having a simple configuration and being inexpensive can be provided.

According to a sixth aspect of the present invention, in the optical sensor system according to any one of the first to fifth aspects, the light emitting device may include a laser light source, and the environmental parameter calculation unit may calculate an oscillation threshold of the laser light source from the value of the second emission light, which is detected by the emission light detector, with reference to a correspondence relation between the detected value of the second emission light and the oscillation threshold of the laser light source, and may calculate the environmental parameter on the basis of the calculated oscillation threshold.

With the features described above, the environmental parameter is calculated on the basis of the oscillation threshold of the light emission in the light emitting device. Therefore, even when the oscillation threshold (oscillation condition) is peculiarly changed, the environmental parameter can be calculated with high accuracy on the basis of the oscillation threshold after being changed.

According to a seventh aspect of the present invention, in the optical sensor system according to any one of the first to sixth aspects, the light emitting device may include a laser light source, and the environmental parameter calculation unit may calculate differential efficiency of the laser light source from the value of the second emission light, which is detected by the emission light detector, with reference to a correspondence relation between the detected value of the second emission light and the oscillation threshold of the laser light source, and may calculate the environmental parameter on the basis of the calculated differential efficiency.

With the features described above, the environmental parameter is calculated on the basis of the differential efficiency of the light emission in the light emitting device. Therefore, even when the differential efficiency (oscillation condition) is peculiarly changed, the environmental parameter can be calculated with high accuracy on the basis of the differential efficiency after being changed.

According to an eighth aspect of the present invention, in the optical sensor system according to any one of the first to seventh aspects, the environmental parameter may be at least one of temperature, humidity, and gas concentration.

With the feature described above, temperature or humidity capable of being utilized in various operations of the optical sensor system can be calculated as the environmental parameter. Furthermore, a concentration of a specific kind of gas affecting any operation and reliability of the light emitting device can be calculated as the environmental parameter.

A ninth aspect of the present invention provides an optical sensor system including a light emitting device that generates first emission light and second emission light, the optical sensor system further including an emission light detector that detects the second emission light, and an environmental parameter calculation unit that calculates an environmental parameter, as an index of an environment around the light emitting device, by employing a value of the second emission light detected by the emission light detector, wherein the light emitting device includes a first light emitting surface from which the first emission light is output, and a second light emitting surface from which the second emission light is output, and the first light emitting surface and the second light emitting surface are constituted such that, when the environmental parameter has changed, a change rate of intensity of the first emission light is smaller than a change rate of intensity of the second emission light.

With the features described above, the intensity of the second emission light exhibits a comparatively large change rate in response to change in the environmental parameter. Therefore, the environmental parameter can be evaluated with high sensitivity on the basis of the intensity of the second emission light. On the other hand, the intensity of the first emission light exhibits a comparatively small change rate in response to change in the environmental parameter. Therefore, the first emission light can be used as an ordinary light source in various applications. As a result, the optical sensor system can be provided which can calculate the environmental parameter, which can be used as a light source, and which has a high added value.

According to a tenth aspect of the present invention, in the optical sensor system according to the ninth aspect, the first light emitting surface and the second light emitting surface may be constituted such that, when the environmental parameter has changed, the change rate of intensity of the first emission light is not more than 1/20 of the change rate of intensity of the second emission light.

With the feature described above, when the environmental parameter has changed, the change rate of intensity of the first emission light is not more than 1/20 of the change rate of intensity of the second emission light. Thus, the second emission light is responsible to the change in the environmental parameter with high sensitivity. Therefore, the environmental parameter can be calculated with high accuracy on the basis of the intensity of the second emission light. On the other hand, the intensity of the first emission light is substantially constant regardless of the change in the environmental parameter. Therefore, the first emission light can be used in a second application without problems even when the environmental parameter has changed.

According to an eleventh aspect of the present invention, in the optical sensor system according to the ninth or tenth aspect, a reflectance of the second light emitting surface on the side facing the interior of the light emitting device may be not less than 85%.

With the feature described above, since the reflectance of the second light emitting surface is high, the oscillation threshold of the light emitting device can be reduced, and power saving in the system can be realized.

Moreover, when the environmental parameter has changed, the intensity of the second emission light is changed to a large extent. The reason is as follows. The large reflectance of the second light emitting surface implies that a transmittance of the second light emitting surface is small. Accordingly, when the environmental parameter has changed, the transmittance of the second light emitting surface is changed to a large extent, and hence the intensity of the second emission light is also changed to a large extent. In other words, the second emission light is responsible to the change in the environmental parameter with high sensitivity. Thus, the environmental parameter can be calculated with high accuracy on the basis of the intensity of the second emission light.

According to a twelfth aspect of the present invention, in the optical sensor system according to any one of the first to eleventh aspects, the optical sensor system may further include a second detector that detects the first emission light, and the environmental parameter calculation unit may correct a calculated result of the environmental parameter on the basis of a value of the first emission light detected by the second detector.

With the features described above, the calculated result of the environmental parameter is corrected on the basis of the detected value of the first emission light. Here, the intensity of the second emission light depends on not only the environmental parameter, but also an output power of the light emitting device. On the other hand, as described above, the intensity of the first emission light hardly depends on the environmental parameter. Thus, the intensity of the first emission light depends on only the output power of the light emitting device.

When the intensity of the second emission light has changed with change in the output power of the light emitting device, the environmental parameter calculated from the intensity of the second emission light includes an error attributable to the change in the output power of the light emitting device. Nevertheless, with the features described above, the calculated result of the environmental parameter can be corrected on the basis of the intensity of the first emission light such that the error attributable to the change in the output power of the light emitting device is eliminated from the calculated result of the environmental parameter. As a result, the highly-accurate environmental parameter after the correction can be obtained.

According to a thirteenth aspect of the present invention, in the optical sensor system according to the twelfth aspect, the environmental parameter calculation unit may control light emission of the light emitting device such that the value of the first emission light detected by the second detector is kept substantially constant.

With the feature described above, the light emission of the light emitting device is controlled such that the detected value of the first emission light is kept substantially constant. Therefore, the first emission light can be stably used in the second application. Furthermore, since the detected value (i.e., the intensity) of the first emission light is kept substantially constant, the intensity of the second emission light is also kept substantially constant. Thus, since the intensity of the second emission light is kept even when the output power of the light emitting device has changed, the environmental parameter can be calculated with high accuracy on the basis of the intensity of the second emission light.

A fourteenth aspect of the present invention provides an optical gas sensor system (100) that may include the optical sensor system according to any one of the first to thirteenth aspects, a gas reactant (110) arranged at a position to which the first emission light is applied, the gas reactant reacting with a specific kind of gas and changing an optical characteristic thereof, a transmitted light detector (130) that detects a part of the first emission light having transmitted through the gas reactant, and a gas detection unit (140) that detects the specific kind of gas contained in the environment by measuring change in the optical characteristic of the gas reactant from a value of the transmitted light detected by the transmitted light detector.

With the features described above, the multi-functional optical gas sensor system can be provided which can not only detect the specific type of gas, but also calculate the environmental parameter.

According to a fifteenth aspect of the present invention, in the optical gas sensor system according to the fourteenth aspect, the gas detection unit may correct a detected result of the specific kind of gas on the basis of a value of the environmental parameter calculated by the environmental parameter calculation unit.

With the feature described above, the detected result of the specific kind of gas obtained with the aid of the gas reactant is corrected on the basis of the calculated value of the environmental parameter. Therefore, even when the optical characteristic of the gas reactant has changed due to change in the environmental parameter, the detected result of the gas can be corrected in such a manner that an influence due to the change in the environmental parameter is eliminated. As a result, the gas can be detected with high accuracy. In addition, the cost of the optical sensor system can be suppressed because of no necessity of including a sensor to measure the environmental parameter.

A sixteenth aspect of the present invention provides a particulate sensor system (200) including the optical sensor system according to any one of the first to thirteenth aspects, a scattered light detector (220) detecting scattered light (260) that is generated upon the first emission light being scattered by particulates (250), and a particulate detection unit (control and arithmetic device 230) that detects the particulates contained in the environment on the basis of a value of the scattered light detected by the scattered light detector.

With the features described above, the multi-functional particulate sensor system can be provided which can not only detect the particulates such as dust, but also calculate the environmental parameter.

A seventeenth aspect of the present invention provides a light emitting apparatus (300) including the optical sensor system according to any one of the first to thirteenth aspects, wherein, assuming that a factor affecting an output power of the emission light generated by the light emitting device is called a light emission condition, the light emitting apparatus further includes a light-emission condition control unit (330) that controls the light emission condition of the light emitting device on the basis of a value of the environmental parameter calculated by the environmental parameter calculation unit.

With the features described above, the occurrence of dew condensation or gas causing a failure of the light emitting device (or a possibility of the occurrence thereof) is determined on the basis of the calculated value of the environmental parameter, and the light emission condition of the light emitting device can be changed on the basis of a result of the determination. When dew condensation or gas causing a failure of the light emitting device has occurred, the light emitting device may be controlled not to emit the light until the cause of the failure is eliminated. Additionally, the cost of the light emitting apparatus can be suppressed because of no necessity of including a sensor to measure the environmental parameter.

An eighteenth aspect of the present invention provides an image printing apparatus (400) including the optical sensor system according to any one of the first to thirteenth aspects, and having an image printing function of forming an electrostatic latent image with the use of the first emission light and printing an image that is obtained by developing the formed electrostatic latent image, wherein, assuming that a factor affecting an output power of the emission light generated by the light emitting device is called a light emission condition, and that a condition specifying an operation or a state of the image printing apparatus in a process of printing the image is called a printing condition, the image printing apparatus further includes a condition control unit (control and arithmetic device 470) that controls at least one of the light emission condition of the light emitting device and the printing condition for the image on the basis of a value of the environmental parameter calculated by the environmental parameter calculation unit.

With the features described above, the electrostatic latent image is formed with the use of the first emission light, and the environmental parameter is calculated with the use of the second emission light. Moreover, at least one of the light emission condition and the printing condition is controlled on the basis of the calculated value of the environmental parameter. Thus, the cost of the image printing apparatus can be suppressed because of no necessity of including a sensor to measure the environmental parameter for the purpose of controlling the light emission condition and the printing condition, both of which depend on the environmental parameter. Examples of the printing condition depending on the environmental parameter include a printed position of an image on the print paper, a feed speed of the print paper, and a heating temperature applied when toner is fixedly fused to the print paper.

The present invention is not limited to the above-described embodiments, and the present invention can be variously modified without departing from the scope defined in Claims. Embodiments obtained by appropriately combining the technical implements, which are disclosed in the above different embodiments, with each other are also included in the technical scope of the present invention.

INDUSTRIAL APPLICABILITY

The present invention can be utilized in optical sensor systems including light sources.

REFERENCE SIGNS LIST 1 optical sensor system
2 optical sensor system
3 optical sensor system
10 semiconductor laser (light emitting device)
20 front surface (second light emitting surface)
21 rear surface (second light emitting surface)
30 front surface outgoing light (first emission light)
31 rear surface outgoing light (second emission light)
40 photodiode (emission light detector)
41 second photodiode (second detector)
60 control and arithmetic device (environmental parameter calculation unit)
80 oscillation threshold
81 differential efficiency
100 optical gas sensor system
110 gas reactant
130 light detector (transmitted light detector)
140 control and arithmetic device (gas detection unit)
150 transmitted light
200 particulate sensor system
220 light detector (scattered light detector)
230 control and arithmetic device (particulate detection unit)
250 particulate
260 scattered light
300 light emitting apparatus
330 control and arithmetic device (light-emission condition control unit)
400 image printing apparatus
470 control and arithmetic device (condition control unit)

The invention claimed is:

1. An optical sensor system comprising:
a light emitting device generating first emission light for use in a predetermined application, the light emitting device further generating second emission light,
an emission light detector detecting the second emission light; and
an environmental parameter calculator calculating an environmental parameter, as an index of an environment around the light emitting device, by employing a value of the second emission light detected by the emission light detector,
wherein the light emitting device includes a laser light source, and
the environmental parameter calculator calculates an oscillation threshold of the laser light source from the value of the second emission light, which is detected by the emission light detector, with reference to a correspondence relation between the detected value of the second emission light and the oscillation threshold of the laser light source, and calculates the environmental parameter on a basis of the calculated oscillation threshold.

2. The optical sensor system according to claim 1, wherein, a factor affecting an output power of the emission light generated by the light emitting device is called a light emission condition,
the light emission condition of the light emitting device when the environmental parameter calculator calculates the environmental parameter is different from the light emission condition when the first emission light output to an exterior is used in the predetermined application.

3. The optical sensor system according to claim 1, wherein at least a part of the emission light generated from the light emitting device when the environmental parameter calculator calculates the environmental parameter is utilized as the first emission light in the predetermined application.

4. The optical sensor system according to claim 1, wherein the environmental parameter calculator calculates the plurality of environmental parameters.

5. The optical sensor system according to claim 1, wherein the environmental parameter calculator calculates the environmental parameter on a basis of the value of the second emission light detected by the emission light detector when a constant amount of current is injected into the light emitting device.

6. The optical sensor system according to claim 1, wherein the light emitting device includes a laser light source, and
the environmental parameter calculator calculates differential efficiency of the laser light source from the value of the second emission light, which is detected by the emission light detector, with reference to a correspondence relation between the detected value of the second emission light and the differential efficiency of the laser light source, and calculates the environmental parameter on a basis of the calculated differential efficiency.

7. The optical sensor system according to claim 1, wherein the environmental parameter is at least one of temperature, humidity, and gas concentration.

8. The optical sensor system according to claim 1, further comprising a second detector that detects the first emission light,
wherein the environmental parameter calculator corrects a calculated result of the environmental parameter on a basis of a value of the first emission light detected by the second detector.

9. The optical sensor system according to claim 8, wherein the environmental parameter calculator controls light emission of the light emitting device such that the value of the first emission light detected by the second detector is kept substantially constant.

10. An optical gas sensor system comprising:
the optical sensor system according to claim 1;
a gas reactant arranged at a position to which the first emission light is applied, the gas reactant reacting with a specific kind of gas and changing an optical characteristic thereof;
a transmitted light detector that detects a part of the first emission light having transmitted through the gas reactant; and
a gas detector that detects the specific kind of gas contained in the environment by measuring change in the optical characteristic of the gas reactant from a value of the transmitted light detected by the transmitted light detector.

11. The optical gas sensor system according to claim 10, wherein the gas detector corrects a detected result of the specific kind of gas on a basis of a value of the environmental parameter calculated by the environmental parameter calculator.

12. A particulate sensor system comprising:
the optical sensor system according to claim 1;
a scattered light detector detecting scattered light that is generated upon the first emission light being scattered by particulates; and a particulate detector that detects the particulates contained in the environment on a basis of a value of the scattered light detected by the scattered light detector.

13. A light emitting apparatus comprising the optical sensor system according to claim 1,
wherein, a factor affecting an output power of the emission light generated by the light emitting device is called a light emission condition,
the light emitting apparatus further comprises a light-emission condition control unit that controls the light emission condition of the light emitting device on a basis of a value of the environmental parameter calculated by the environmental parameter calculator.

14. An optical sensor system comprising:
a light emitting device generating first emission light and second emission light,
an emission light detector detecting the second emission light; and
an environmental parameter calculator calculating an environmental parameter, as an index of an environment around the light emitting device, by employing a value of the second emission light detected by the emission light detector,
wherein the light emitting device includes a first light emitting surface from which the first emission light is output, and a second light emitting surface from which the second emission light is output, and
the first light emitting surface and the second light emitting surface are constituted such that, when the environmental parameter has changed, a change rate of intensity of the first emission light is smaller than a change rate of intensity of the second emission light,
wherein the light emitting device includes a laser light source, and
the environmental parameter calculator calculates an oscillation threshold of the laser light source from the value of the second emission light, which is detected by the emission light detector, with reference to a correspondence relation between the detected value of the second emission light and the oscillation threshold of the laser light source, and calculates the environmental parameter on a basis of the calculated oscillation threshold.

15. The optical sensor system according to claim 14, wherein the first light emitting surface and the second light emitting surface are constituted such that, when the environmental parameter has changed, the change rate of intensity of the first emission light is not more than 1/20 of the change rate of intensity of the second emission light.

16. The optical sensor system according to claim 14, wherein a reflectance of the second light emitting surface on a side facing an interior of the light emitting device is not less than 85%.

17. An image printing apparatus comprising an optical sensor system and having an image printing function of forming an electrostatic latent image with use of the first emission light and printing an image that is obtained by developing the formed electrostatic latent image,
wherein the optical sensor system comprising:
a light emitting device generating first emission light for use in a predetermined application, and the light emitting device generating second emission light,
an emission light detector detecting the second emission light; and
an environmental parameter calculator calculating an environmental parameter, as an index of an environment around the light emitting device, by employing a value of the second emission light detected by the emission light detector
wherein, a factor affecting an output power of the emission light generated by the light emitting device is called a light emission condition, and that a condition specifying an operation or a state of the image printing apparatus in a process of printing the image is called a printing condition,
the image printing apparatus further comprises a condition control unit that controls at least one of the light emission condition of the light emitting device and the printing condition for the image on a basis of a value of the environmental parameter calculated by the environmental parameter calculator.

* * * * *